US009068018B2

(12) United States Patent
Ramsey et al.

(10) Patent No.: US 9,068,018 B2
(45) Date of Patent: Jun. 30, 2015

(54) METHODS OF USING VOLTAGE-GATED HV1 PROTON CHANNELS TO DETECT CHANGES IN INTRACELLULAR PH

(75) Inventors: Ian S. Ramsey, Jamaica Plain, MA (US); Magdalene M. Moran, Brookline, MA (US); Jayhong A. Chong, Brookline, MA (US); David Clapham, Wellesley, MA (US)

(73) Assignee: Children's Medical Center Corporation, Boston, MA (US)

( * ) Notice: Subject to any disclaimer, the term of this patent is extended or adjusted under 35 U.S.C. 154(b) by 1867 days.

(21) Appl. No.: 12/279,436

(22) PCT Filed: Feb. 15, 2007

(86) PCT No.: PCT/US2007/062253
§ 371 (c)(1),
(2), (4) Date: Jan. 19, 2010

(87) PCT Pub. No.: WO2007/095625
PCT Pub. Date: Aug. 23, 2007

(65) Prior Publication Data
US 2012/0270236 A1 Oct. 25, 2012

Related U.S. Application Data

(60) Provisional application No. 60/773,398, filed on Feb. 15, 2006, provisional application No. 60/777,758, filed on Mar. 1, 2006.

(51) Int. Cl.
| | |
|---|---|
| G01N 33/567 | (2006.01) |
| G01N 33/53 | (2006.01) |
| G01N 33/569 | (2006.01) |
| G01N 33/554 | (2006.01) |
| C12N 1/20 | (2006.01) |
| C12N 1/00 | (2006.01) |
| C12N 5/00 | (2006.01) |
| C12N 5/02 | (2006.01) |
| C12N 5/07 | (2010.01) |
| C12N 5/10 | (2006.01) |
| C07K 14/705 | (2006.01) |
| G01N 33/68 | (2006.01) |

(52) U.S. Cl.
CPC .......... *C07K 14/705* (2013.01); *G01N 33/6872* (2013.01)

(58) Field of Classification Search
CPC ..................... C07K 14/705; G01N 33/6872
See application file for complete search history.

(56) References Cited

U.S. PATENT DOCUMENTS

2003/0171275 A1* 9/2003 Baughn et al. .................. 514/12

OTHER PUBLICATIONS

Green, 1988, Journal of Neurophysiology, vol. 59, Issue 1, pp. 248-258.*
Madshus, 1988, Biochemical Journal, vol. 250, pp. 1-8.*
Rogl, 1998, FEBS Letters, vol. 432, pp. 21-26.*
Ramsey et al. "A Voltage-Gated Proton-Selective Channel Lacking the Pore Domain," Nature 2006, vol. 440. No. 27, pp. 1213-1216.
Sasaki et al. "A Voltage Sensor-Domain Protein is a Voltage-Gated Proton Channel," Science Apr. 2006, vol. 312, pp. 589-592.
Lee et al. "Dimeric Subunit Stoichiometry of the Human Voltage-Dependent Proton Channel Hv1" PNAS Jun. 2008, vol. 105. No. 22, pp. 7692-7695.
Tombola et al. "The Voltage-Gated Proton Channel Hv1 Has Two Pores, Each Controlled by One Voltage Sensor," Neuron, May 2008, vol. 58, pp. 546-556.
DeCoursey, "Hydrogen ion currents in rat alveolar epithelial cells," Biophys. J. 60:1243-53 (1991).
DeCoursey, "Voltage-Gated proton Channels and other Proton Transfer Patways," Physiol. Rev. 83:475-579 (2003).
Diarra et al., "Anoxia-evoked intracellular pH and $Ca^{2+}$ concentration changes in cultured postnatal rat hippocampal neurons," Neuroscience 93:1003-16 (1999).
Eder and DeCoursey, "Voltage-gated proton channels in microglia," Prog. Neurobiol. 64:277-305 (2001).
Henderson et al., "The superoxide-generating NADPH oxidase of human neutrophils is electrogenic and associated with an $H^+$ Channel," Biochem. J. 246:325-9 (1997).
Jiang et al., "X-ray structure of a voltage-dependent K+ Channel," (2003), Nature 423:33-41.
Kapus et al., "A Ph-sensitive and Voltage-dependent Proton Conductance in the plasma membrane of Macrophages," J. Gen. Physiol. 102:729-760 (1993).
Krause et al., "Human skeletal muscle has avoltage-gated proton current," Neuromuscul. Disord. 3:407-11 (1993).
Long et al, "Crystal structure of a mammalian voltage-dependent shker family K= channel," (2005a), Science 309(5736):897-903.
Long et al., "Voltage Sensor of Kv. 1.2: Structural basis of Electromechanical coupling," (2005b), Science 309(5736):903-8.
Morgan et al., "Absence of Proton Channels in COS-7 Cells Expressing Functional NADPH Oxidase Components," J. Gen. Physiol. 119: 571-580 (2002).
Murata et al., "Phosphoinositide phosphatase activity coupled to an intrinsic voltage sensor," Nature 435: 1239-1243 (2005).
Murphy and DeCoursey, "Charge compensation during the phagocyte respiratory burst," (2006), Biochim. Biophys. Acta 1757(8):996-1011.
Myers et al., "Detection of single base substitutions by ribonuclease cleavage at mismatches in RNA: DNA Duplexes," Science 230:1242 (1985).
Nordstrom et al., "Regulation of Cytoplasmic pH in Osteoclasts," J. Biol. Chem. 270: 2203-12 (1995).
Peralta et al., "differential reguulation of PI hydrolysis and adenylyl cyclase by muscarinic receptor subtypes," Nature 334: 434-7 (1988).
Schilling et al., "Voltage-activated proton currents in human lymphocytes," J. Physiol. 545:93-105 (2002).

(Continued)

Primary Examiner — Robert Landsman
(74) Attorney, Agent, or Firm — Fish & Richardson P.C.

(57) ABSTRACT

Nucleic acid and protein sequences relating to a proton channel (Hv1) are disclosed. Nucleic acids, vectors, transformed cells, transgenic animals, polypeptides, and antibodies relating to the Hv1 gene and protein are disclosed. Also provided are methods of identifying modulators of Hv1 activity, methods of geno typing subjects with respect to Hv1, and methods of diagnosing and treating Hv1-mediated disorders.

16 Claims, 6 Drawing Sheets

(56) References Cited

OTHER PUBLICATIONS

Sheldon and Church, "Intracellular pH Response to Anoxia in Acutely Dissociated Adult Rat Hippocampal CA1 Neurons," J. Neurophysiol. 87:2209-24 (2002).
Smith and Curnutte, "Molecular Basis of Chronic Granulomatous Disease," Blood 77:673-86 (1991).
Thomas et al., "Hydrogen ion currents and intracellular pH in depolarized voltage-clamped snail neurones," Nature 299: 826-8 (1982).
International Preliminary Report on Patentability issued in PCT/US2007/062253 on Nov. 27, 2008 (5 pages).
International Search Report issued for PCT/US07/62253, dated Oct. 21, 2008.

* cited by examiner

Figure 2

*Hv1 protein sequence alignment*

```
  1 MATWDEKAVTRRAKVAPAERMSKFLRHFTVVGDDYHAWNINYKKWENEEEEEEEQPPPTP-VSGEEGRAAAPDV  Homo sapiens
  1 MATWDEKAVTRRAKVAPAERMSKFLKHFTVVGDDYHAWNINYKKWENEEDEEEEQPPPTP-ASGEEGRVAGPDA  Macaca mulatta
  1 MATWNEKAVTRRARVAPAERMSKFLKHFTVVGDDYHAWNINYKKWENEEEEEEQPPPTEASASAEEGRATDF--  Bos taurus
  1 MATWDEKASSRRARVAPAERMSKFLKHFTVVGDDYHAWNVNYKKWENEEDDEEEEQPPPTA-ASGEEGRAD----  Canis familiaris
  1 MAKQG-EAVTRRTKVAPTKRMSRFLKHFTVVGDDYHTWNVNYKKWENEEDEEE-----PAPTSAEGEGSAVGPDA  Rattus norvegicus
  1 MTSHDPKAVTRRTKVAPTKRMSRFLKHFTVVGDDYHTWNVNYKKWENEEEEEE-----PAPTSAEGEGNAEGPDA  Mus musculus
  1 M-------------------SRYLKHFTVVGDDPIQWSNDYQKWENEEEDNGEKDSEIKLEPS-----------  Gallus gallus
  1 MA-----------------GCLRHFTSVGDD----TKK-KAWKEEDVEVAHEEEPKNT-----------PHP   Xenopus tropicalis
  1 MA-----------------GCLRHFTSVGDD----TKK-REWKQEDVEVAYEEPLKNT-----------PHP   Xenopus laevis
  1 MS-----------------RYLKHFTAVGDN----KSAVPTWHEEDTS-HHVTTLHDA-----------PDG   Danio rerio
  1 MS-----------------YLS---------------------------------------------------  Ciona intestinalis

[S1]                            [S2]
 75 APAPGPAPRAPLDFRGMLRKLFSSHRFQVIIICLVVLDALLVLAELILDLKIIQPDKNNYAAMVFHYMSITILVF  Homo sapiens
 75 APAPGPAPRAPLDFRGTLRKLFSSHRFQVIIICLVVLDTLLVLAELILDLRIIQPDKNYAAMIFHYMSIAILAL  Macaca mulatta
 74 TPAPAPVPRFRLDFRTTLRKLFSAHRFQVIIICLVVLDALLVLAELVLDLKIIEPDKNNYAPKVFHYMSLAILTF  Bos taurus
 71 -PTAAPTPRPPLDFRATLRKLFSSHRFQVIIICLVILDALLVLAELILDLKIIQGDKNNYATKVFHYSSPAILTL  Canis familiaris
 70 EAGSASTPRPSLDFKRSRLRKLFSSHRFQVIIICLVVLDALLVLAELLLDLRIIEPDLSKYSTKVFHYLSLAIAF  Rattus norvegicus
 71 EAGSASTPRQSLDFRSRLRKLFSSHRFQVIIICLVVLDALLVLAELLLDLKIIEPDEQDYAVTAFHYMSFAILVF  Mus musculus
 45 --------RGHVTFQDVMKKLFSSRRFQIVIVFLVIVDALLVLGELLMDLKIIHPDKYHIAPKVFHYLSLSILTI  Gallus gallus
 40 F-------IASYSFRGALKWLFSSHKFQIVIICLVILDALFVLVEVLLDLELLAEKVDHIIPELFHYLSISVLSF  Xenopus tropicalis
 40 F-------IASYSFRGALKWLLSSHKFQIVIICLVIIDALFVLVEVLLDLELLAEKVDHIIPEIFHYLSISVLTF  Xenopus laevis
 40 LEVSTGQHLGQLSFRDSLRKLYSTERFQIVVVCLVVLDAIFVLCELLIDLSIIEADHHRIAPQVPHYLSLALLTF  Danio rerio
  6 ----------------------FQVATIVLVVLDSFLVVGELLIDLKVIIVPHGNPAPELLHGFSLSILSI    Ciona intestinalis

[S2]                    [S3]                          [S4]
150 FMMEIIFKLFVFRLEFFHHKFEILDAVVVVVSFILDIVLLF--QEHQFEALGLLILLRLWRVARIINGIIISVKT  Homo sapiens
150 FMMEITFKLFVFRLEFFHHKFEILDAVVVVVSFVLDVVLLF--QEHEFEALGLLILLRLWRVARIINGIIISVKT  Macaca mulatta
149 FMMEIFFKIFVFRLEFFHHKFEILDTIVVVVISFILDLVLLF--REHQFEALGLLILLRLWRVARIINGIIISVKT  Bos taurus
145 FMMEVFLKIFVFRLEFFHHKFEILDTFVVVVSFILDLVLLF--QKHEFEALGLLILLRLWRVARIINGIIISVKT  Canis familiaris
145 FVLEISLKVFVFRLEFFHHKFEILDAIVVVVSFVLDLILLF--KNHHFEALGLLILLRLWRVARIINGIIISVKT  Rattus norvegicus
146 FMLEIFFKIFVFRLEFFHHKFEILDAFVVVVSFVLDLVLLF--KSHHFEALGLLILLRLWRVARIINGIIISVKT  Mus musculus
112 FLVEVGFKIFVYGREFFHHKFEVLDSIVVVVSFILDLVLLF--REHEFEAVGLLILLRLWRVARIINGIIISVKT  Gallus gallus
108 FILEIAGKLYAFRLEFFHHKFEVFDAAIVVISFIIDIVYIS--REDIFNAVGLLILLRLWRVARIVNGIIVSVKT  Xenopus tropicalis
108 FILEIAGKIYAFRLEFFHHKFEVFDAAIVVISFIIDIVYIS--REDIFNAVGLLILLRLWRVARIVNGVIVSVKT  Xenopus laevis
115 FMVELAGKIFAYRLEFLHHKFEVFDGIVVVVSFILDIIYIS--KEDAFDAMGLLILLRLWRVARIINGILVSVQN  Danio rerio
 55 FMVEIALKILADHRHFIHHKVEVLDAVVVVISFGVDIALIFVGESEALAAIGLLVILRLWRVFRIINGIIVTVKT  Ciona intestinalis 223 RSERQLLRLKQMNVQLAAKTQHLEFSCSEKEQEIERLNKLLRQHG--------LLGEVN.  Homo sapiens
223 RSERQLLRLKQMNVQLAAKIQHLEFSCSEKEQEIERLNKLLRQHG--------LLGEVN.  Macaca mulatta
222 RSERQLLRLKQINIQLATKIQHLEFSCSEKEQEIERLNKLLRQHG--------LLGEVN.  Bos taurus
218 RSERQLLRLKQMNIQLAAKIQHLEFSCSEKEQEIERLNKLLRQHG--------LLGEVN.  Canis familiaris
218 RSERQILRLKQINLQLATKIQHLEFSCSEKEQEIERLSKLLRQNG--------LLEDVNVN.  Rattus norvegicus
219 RSERQILRLKQINIQLATKIQHLEFSCSEKEQEIERLNKLLKQNG--------LLGDVN.  Mus musculus
185 RSEQQVSKLKQVNLKLATKVEQLQHSCVEKEQEIERLTRMLKQHG--------LLSEQT.  Gallus gallus
181 QAEDKIHRLKENQESLLEKVAHLEQQCAQQEQEIVRLQTLLQQHN--------VFPA---S.  Xenopus tropicalis
181 RAEEKMHKLKEQKGSLLEKVAQLEQQCAQQEQEIGRLHKLLQEHN--------VFPA---S.  Xenopus laevis
188 RANHRVEKLKEINESLVHQVNELKEQNTKMDQENVRLRALLKDHS--------I--D---F.  Danio rerio
130 KADDRVHEIKKKNSELELQIHNLFEKLSQKEQDMSRLHEILRCNNIDIPPTVPLTTSVQIHSTTTASADV.  Ciona intestinalis
```

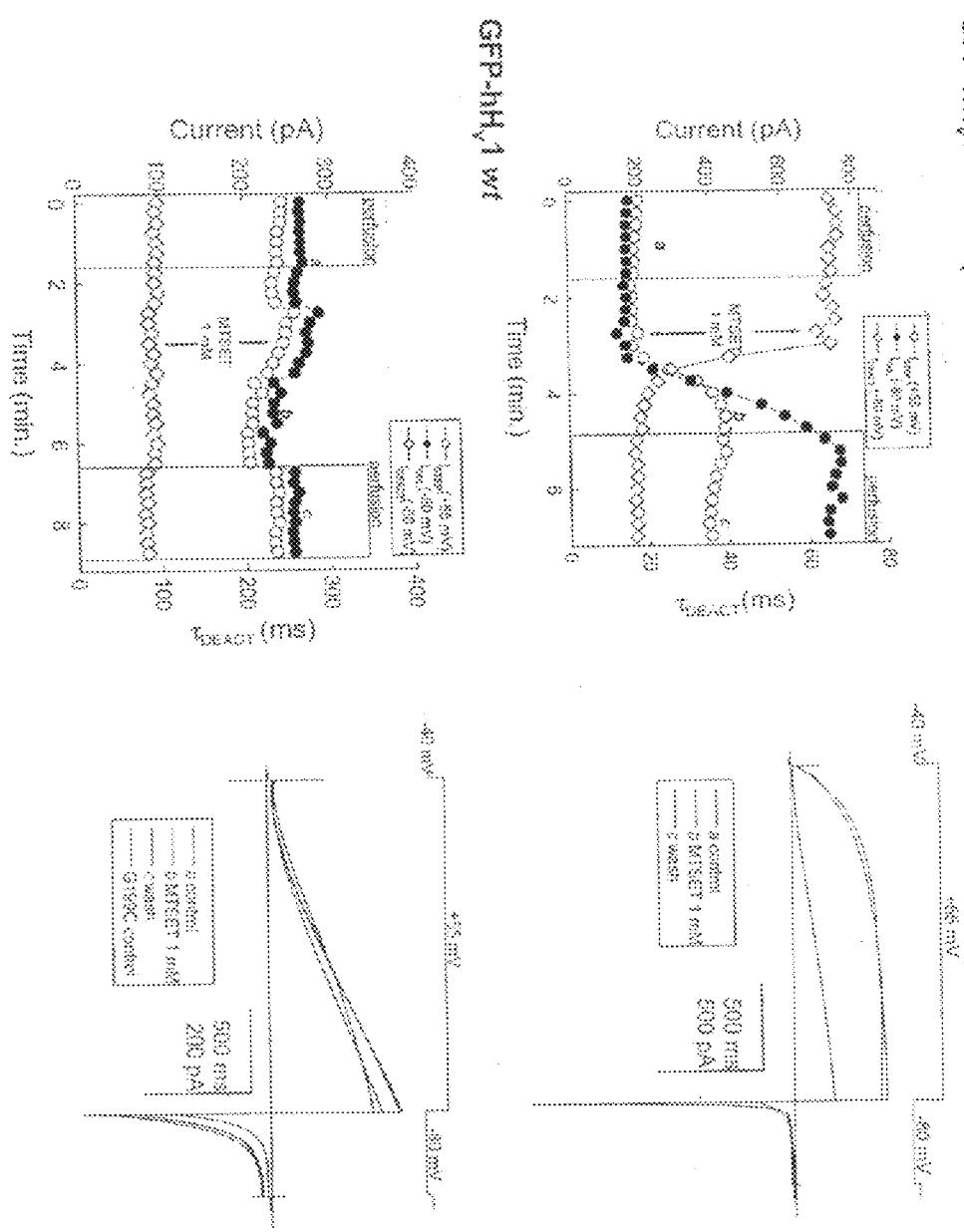

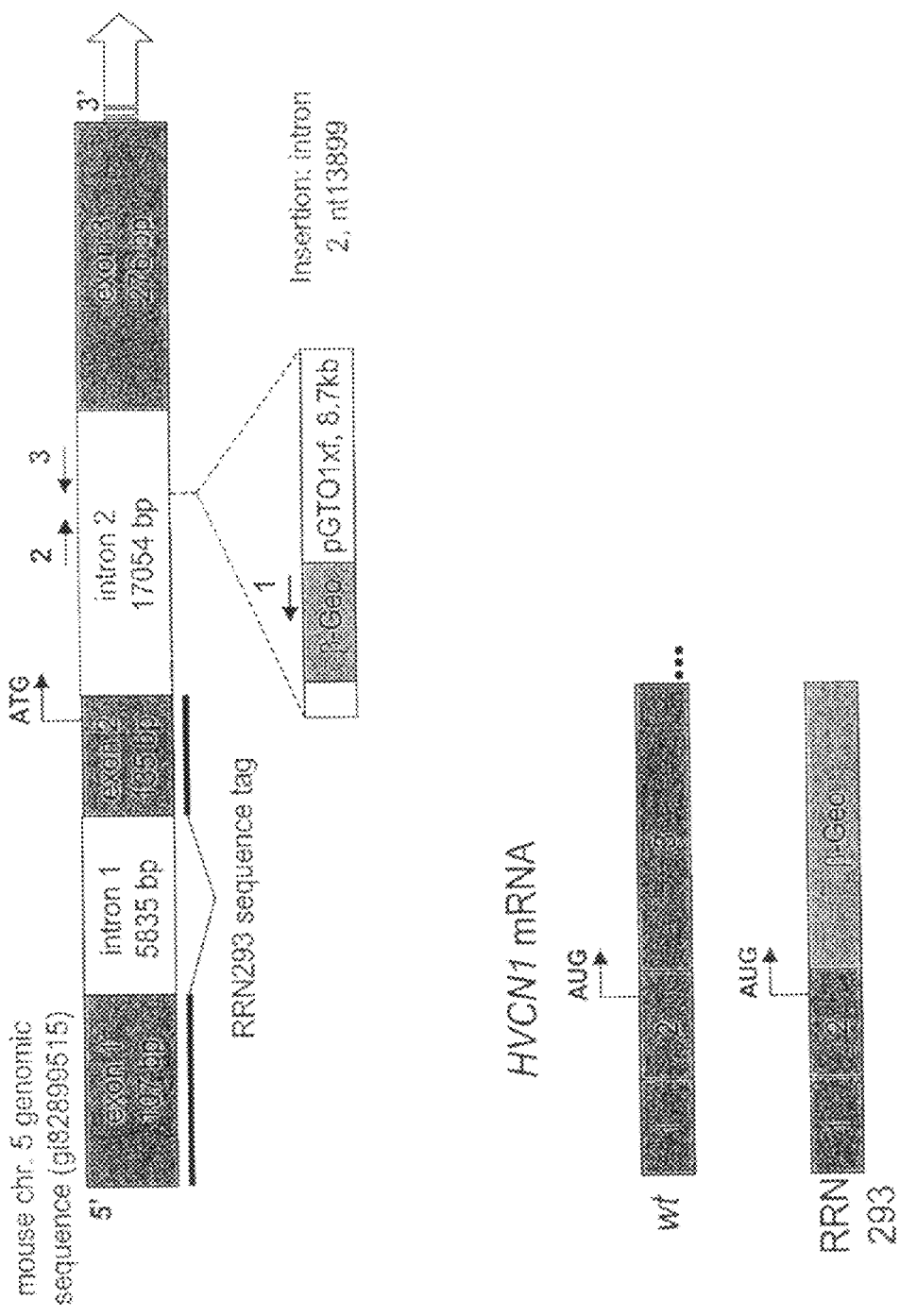

SEQUENCE LISTING

```
<160> NUMBER OF SEQ ID NOS: 23

<210> SEQ ID NO 1
<211> LENGTH: 822
<212> TYPE: DNA
<213> ORGANISM: Homo sapiens

<400> SEQUENCE: 1
atggccacct gggacgaaaa ggcagtcacc cgcagggcca aggtggctcc cgctgagagg      60
atgagcaagt tcttaaggca cttcacggtc gtgggagacg actaccatgc ctggaacatc     120
aactacaaga aatgggagaa tgaagaggag gaggaggagg aggagcagcc accacccaca     180
ccagtctcag gcgaggaagg cagagctgca gcccctgacg ttgcccctgc ccctggcccc     240
gcacccaggg cccccttga cttcaggggc atgttgagga aactgttcag ctcccacagg     300
tttcaggtca tcatcatctg cttggtggtt ctggatgccc tcctggtgct tgctgagctc     360
atcctggacc tgaagatcat ccagcccgac aagaataact atgctgccat ggtattccac     420
tacatgagca tcaccatctt ggtcttttt atgatggaga tcatctttaa attatttgtc     480
ttccgcctgg agttctttca ccacaagttt gagatcctgg atgccgtcgt ggtggtggtc     540
tcattcatcc tcgacattgt cctcctgttc caggagcacc agtttgaggc tctgggcctg     600
ctgattctgc tccggctgtg gcgggtggcc cggatcatca tgggattat catctcagtt     660 aagacacgtt cagaacggca actcttaagg ttaaaacaga tgaatgtaca attggccgcc     720
aagattcaac accttgagtt cagctgctct gagaaggaac aagaaattga aagacttaac     780
aaactattgc gacagcatgg acttcttggt gaagtgaact ag                        822

<210> SEQ ID NO 2
<211> LENGTH: 273
<212> TYPE: PRT
<213> ORGANISM: Homo sapiens
```

<400> SEQUENCE: 2

```
Met Ala Thr Trp Asp Glu Lys Ala Val Thr Arg Arg Ala Lys Val Ala
 1               5                  10                  15
Pro Ala Glu Arg Met Ser Lys Phe Leu Arg His Phe Thr Val Val Gly
                20                  25                  30
Asp Asp Tyr His Ala Trp Asn Ile Asn Tyr Lys Lys Trp Glu Asn Glu
            35                  40                  45
Glu Glu Glu Glu Glu Gln Pro Pro Thr Pro Val Ser Gly
        50                  55                  60
Glu Glu Gly Arg Ala Ala Ala Pro Asp Val Ala Pro Ala Pro Gly Pro
 65                  70                  75                  80
Ala Pro Arg Ala Pro Leu Asp Phe Arg Gly Met Leu Arg Lys Leu Phe
                85                  90                  95
Ser Ser His Arg Phe Gln Val Ile Ile Ile Cys Leu Val Val Leu Asp
                100                 105                 110
Ala Leu Leu Val Leu Ala Glu Leu Ile Leu Asp Leu Lys Ile Ile Gln
            115                 120                 125
Pro Asp Lys Asn Asn Tyr Ala Ala Met Val Phe His Tyr Met Ser Ile
130                 135                 140
Thr Ile Leu Val Phe Phe Met Met Glu Ile Ile Phe Lys Leu Phe Val
145                 150                 155                 160
Phe Arg Leu Glu Phe Phe His His Lys Phe Glu Ile Leu Asp Ala Val
                165                 170                 175
Val Val Val Val Ser Phe Ile Leu Asp Ile Val Leu Leu Phe Gln Glu
            180                 185                 190
His Gln Phe Glu Ala Leu Gly Leu Leu Ile Leu Leu Arg Leu Trp Arg
        195                 200                 205
Val Ala Arg Ile Ile Asn Gly Ile Ile Ile Ser Val Lys Thr Arg Ser
    210                 215                 220
Glu Arg Gln Leu Leu Arg Leu Lys Gln Met Asn Val Gln Leu Ala Ala
225                 230                 235                 240
Lys Ile Gln His Leu Glu Phe Ser Cys Ser Glu Lys Glu Gln Glu Ile
                245                 250                 255
Glu Arg Leu Asn Lys Leu Leu Arg Gln His Gly Leu Leu Gly Glu Val
            260                 265                 270
Asn
```

<210> SEQ ID NO 3
<211> LENGTH: 822
<212> TYPE: DNA
<213> ORGANISM: Macaca mulatta

<400> SEQUENCE: 3

```
atggccacct gggacgagaa ggcagtcacc cgcagggcca aggtggctcc cgctgagagg     60
atgagcaagt tcttaaagca cttcacggtc gtagggacg actaccatgc ctggaacatc    120
aactacaaga atgggagaa tgaagaggac gaggaggagg aggaacagcc gccacccaca    180
ccagcctcgg gcgaggaagg cagagttgca ggccctgacg ctgccctgc cctggcccc     240
gcgcccaggg ccccccttga cttcaggggc acgttgagga aactgttcag ctcccacagg    300
tttcaggtca tcatcatctg cttggtggtt ctggacaccc tcctggtgct tgctgagctc    360
atcctggacc tgaggatcat ccagcccgac aagaaaaact atgccgccat gatattccac    420
tacatgagca tcgccatctt ggccctttt atgatggaga ttacctttaa attatttgtc    480
```

```
ttccgcctgg agttctttca ccacaagttt gagatcctgg atgccgtcgt ggtggtggtc    540
tcattcgtcc tcgacgttgt cctcctgttc caggagcacg agtttgaggc tctgggcctg    600
ctgattctgc ttcggctgtg gcgggtggcc cggatcatca cgggattat catctcagtt     660 aagacacgtt cagaacggca actcttaagg ttaaaacaga tgaatgtaca attggccgcc    720
aagattcaac accttgagtt cagctgctct gagaaggaac aagaaattga aagacttaac    780
aagctattgc gacagcatgg acttcttggt gaagtgaact ag                       822
```

<210> SEQ ID NO 4
<211> LENGTH: 273
<212> TYPE: PRT
<213> ORGANISM: Macaca mulatta

<400> SEQUENCE: 4

```
Met Ala Thr Trp Asp Glu Lys Ala Val Thr Arg Arg Ala Lys Val Ala
 1               5                  10                  15

Pro Ala Glu Arg Met Ser Lys Phe Leu Lys His Phe Thr Val Val Gly
            20                  25                  30

Asp Asp Tyr His Ala Trp Asn Ile Asn Tyr Lys Lys Trp Glu Asn Glu
        35                  40                  45

Glu Asp Glu Glu Glu Glu Gln Pro Pro Thr Pro Ala Ser Gly
    50                  55                  60

Glu Glu Gly Arg Val Ala Gly Pro Asp Ala Ala Pro Ala Pro Gly Pro
65                  70                  75                  80

Ala Pro Arg Ala Pro Leu Asp Phe Arg Gly Thr Leu Arg Lys Leu Phe
                85                  90                  95

Ser Ser His Arg Phe Gln Val Ile Ile Ile Cys Leu Val Val Leu Asp
            100                 105                 110

Thr Leu Leu Val Leu Ala Glu Leu Ile Leu Asp Leu Arg Ile Ile Gln
        115                 120                 125

Pro Asp Lys Lys Asn Tyr Ala Ala Met Ile Phe His Tyr Met Ser Ile
    130                 135                 140

Ala Ile Leu Ala Leu Phe Met Met Glu Ile Thr Phe Lys Leu Phe Val
145                 150                 155                 160

Phe Arg Leu Glu Phe Phe His His Lys Phe Glu Ile Leu Asp Ala Val
                165                 170                 175

Val Val Val Val Ser Phe Val Leu Asp Val Val Leu Leu Phe Gln Glu
            180                 185                 190

His Glu Phe Glu Ala Leu Gly Leu Leu Ile Leu Leu Arg Leu Trp Arg
        195                 200                 205

Val Ala Arg Ile Ile Asn Gly Ile Ile Ile Ser Val Lys Thr Arg Ser
    210                 215                 220

Glu Arg Gln Leu Leu Arg Leu Lys Gln Met Asn Val Gln Leu Ala Ala
225                 230                 235                 240

Lys Ile Gln His Leu Glu Phe Ser Cys Ser Lys Glu Gln Glu Ile
                245                 250                 255

Glu Arg Leu Asn Lys Leu Leu Arg Gln His Gly Leu Leu Gly Glu Val
            260                 265                 270

Asn
```

<210> SEQ ID NO 5
<211> LENGTH: 819
<212> TYPE: DNA
<213> ORGANISM: Bos taurus

<400> SEQUENCE: 5

```
atggccacgt ggaatgaaaa ggcagtcacc cgcagggcca gggtggctcc cgccgagagg      60
atgagcaagt tcttgaaaca cttcaccgtc gtcggggacg actaccacgc ctggaacatc     120
aactacaaga gtgggaaaaa tgaggaggag gaggaagaag agcagccacc gcccactgag     180
gcctcagcct cggccgagga gggcagagcc actgacccca ccccggcccc ggcccctgtg     240
cccaggcccc gcctagactt caggaccact ttgaggaagc tcttcagcgc ccacaggttt     300
caggttatca tcatctgcct ggtcgtcctg gatgccctcc tggtgctcgc agagctcgtt     360
ttggacctga agatcatcga gcccgacaag aataactatg cccccaaggt gttccactac     420
atgagccttg ccatcctaac cttttttatg atggagattt tctttaaaat atttgtcttc     480
cgcttggagt tctttcacca caagtttgaa atcctggaca ccatcgtggt ggtcatttcc     540
ttcatcctcg acctcgtcct cctgttccgg gagcatcaat tcgaggctct aggactgctg     600
atcctgctcc ggctgtggcg ggtggcccgg atcatcaatg ggataattat ctcagttaag     660
acacgttcag aacggcaact gttaaggtta aaacagataa acatacaact ggccaccaag     720
atccagcacc ttgaattcag ctgctctgag aaggaacaag aaattgagag acttaacaag     780
ctattgagac agcatggact tctcggagaa gtgaactag                            819
```

<210> SEQ ID NO 6
<211> LENGTH: 272
<212> TYPE: PRT
<213> ORGANISM: Bos taurus

<400> SEQUENCE: 6

```
Met Ala Thr Trp Asn Glu Lys Ala Val Thr Arg Arg Ala Arg Val Ala
  1               5                  10                  15
Pro Ala Glu Arg Met Ser Lys Phe Leu Lys His Phe Thr Val Val Gly
                 20                  25                  30
Asp Asp Tyr His Ala Trp Asn Ile Asn Tyr Lys Lys Trp Glu Asn Glu
             35                  40                  45
Glu Glu Glu Glu Glu Gln Pro Pro Thr Glu Ala Ser Ala Ser
 50                  55                  60
Ala Glu Glu Gly Arg Ala Thr Asp Pro Thr Pro Ala Pro Ala Pro Val
 65                  70                  75                  80
Pro Arg Pro Arg Leu Asp Phe Arg Thr Thr Leu Arg Lys Leu Phe Ser
                 85                  90                  95
Ala His Arg Phe Gln Val Ile Ile Ile Cys Leu Val Val Leu Asp Ala
            100                 105                 110
Leu Leu Val Leu Ala Glu Leu Val Leu Asp Leu Lys Ile Ile Glu Pro
        115                 120                 125
Asp Lys Asn Asn Tyr Ala Pro Lys Val Phe His Tyr Met Ser Leu Ala
    130                 135                 140
Ile Leu Thr Phe Phe Met Met Glu Ile Phe Phe Lys Ile Phe Val Phe
145                 150                 155                 160
Arg Leu Glu Phe Phe His His Lys Phe Glu Ile Leu Asp Thr Ile Val
                165                 170                 175
Val Val Ile Ser Phe Ile Leu Asp Leu Val Leu Leu Phe Arg Glu His
            180                 185                 190
Gln Phe Glu Ala Leu Gly Leu Leu Ile Leu Leu Arg Leu Trp Arg Val
        195                 200                 205
Ala Arg Ile Ile Asn Gly Ile Ile Ile Ser Val Lys Thr Arg Ser Glu
```

```
                210                 215                 220
Arg Gln Leu Leu Arg Leu Lys Gln Ile Asn Ile Gln Leu Ala Thr Lys
225                 230                 235                 240

Ile Gln His Leu Glu Phe Ser Cys Ser Glu Lys Glu Gln Glu Ile Glu
                245                 250                 255

Arg Leu Asn Lys Leu Leu Arg Gln His Gly Leu Leu Gly Glu Val Asn
                260                 265                 270

<210> SEQ ID NO 7
<211> LENGTH: 807
<212> TYPE: DNA
<213> ORGANISM: Canis familiaris

<400> SEQUENCE: 7
atggccacct gggatgaaaa ggccagctcc cgcagggcca gagtggctcc ggccgaaagg    60
atgagcaagt tcctgaagca cttcactgtc gttggggacg attaccatgc ctggaatgtc   120
aactataaga atgggagaa tgaggaggac gatgaagagg aggagcagcc gccaccaaca   180
gctgcctcgg gcgaggaggg cagagccgac cccactgcgg cccccacgcc caggcccccc   240
ctcgacttca gggccacatt aaggaagctc ttcagctccc acaggtttca ggttatcatc   300
atctgcctgg tcattctgga tgccctcctg gtgctggccg agctcattct ggacctgaag   360
atcatccagg gtgacaagaa taactatgcc accaaggtgt ccactactc aagctttgcc    420 atcttgacgc tttttatgat ggaggttttt ttaaaattat ttgtcttccg cttggagttc   480
tttcaccaca aatttgaaat cctggacacc tttgtggtgg tggtttcctt catcctcgac   540
cttgtcctcc tgttccagaa gcatgagttt gaggctcttg ggctgctgat tctgctccgg   600
ctgtggcggg tggcccggat catcaacgga taattatct cggtaaagac acgttcagaa    660
cgacaactgc tgaggttaaa acagatgaat atacagttgg ccgccaagat ccaacacctt   720
gaattcagct gctctgagaa ggaacaagaa attgaaagac tgaacaagct attgagacag   780
catggacttc ttggtgaagt caactag                                        807

<210> SEQ ID NO 8
<211> LENGTH: 268
<212> TYPE: PRT
<213> ORGANISM: Canis familiaris

<400> SEQUENCE: 8

Met Ala Thr Trp Asp Glu Lys Ala Ser Ser Arg Arg Ala Arg Val Ala
1               5                   10                  15

Pro Ala Glu Arg Met Ser Lys Phe Leu Lys His Phe Thr Val Val Gly
                20                  25                  30

Asp Asp Tyr His Ala Trp Asn Val Asn Tyr Lys Lys Trp Glu Asn Glu
            35                  40                  45

Glu Asp Asp Glu Glu Glu Glu Gln Pro Pro Thr Ala Ala Ser Gly
50                  55                  60

Glu Glu Gly Arg Ala Asp Pro Thr Ala Ala Pro Thr Pro Arg Pro Pro
65                  70                  75                  80

Leu Asp Phe Arg Ala Thr Leu Arg Lys Leu Phe Ser Ser His Arg Phe
                85                  90                  95

Gln Val Ile Ile Ile Cys Leu Val Ile Leu Asp Ala Leu Leu Val Leu
            100                 105                 110

Ala Glu Leu Ile Leu Asp Leu Lys Ile Ile Gln Gly Asp Lys Asn Asn
            115                 120                 125
```

```
Tyr Ala Thr Lys Val Phe His Tyr Ser Ser Phe Ala Ile Leu Thr Leu
            130                 135                 140

Phe Met Met Glu Val Phe Leu Lys Leu Phe Val Phe Arg Leu Glu Phe
145                 150                 155                 160

Phe His His Lys Phe Glu Ile Leu Asp Thr Phe Val Val Val Ser
                165                 170                 175

Phe Ile Leu Asp Leu Val Leu Leu Phe Gln Lys His Glu Phe Glu Ala
                180                 185                 190

Leu Gly Leu Leu Ile Leu Leu Arg Leu Trp Arg Val Ala Arg Ile Ile
            195                 200                 205

Asn Gly Ile Ile Ile Ser Val Lys Thr Arg Ser Glu Arg Gln Leu Leu
    210                 215                 220

Arg Leu Lys Gln Met Asn Ile Gln Leu Ala Ala Lys Ile Gln His Leu
225                 230                 235                 240

Glu Phe Ser Cys Ser Glu Lys Glu Gln Glu Ile Glu Arg Leu Asn Lys
                245                 250                 255

Leu Leu Arg Gln His Gly Leu Leu Gly Glu Val Asn
            260                 265
```

```
<210> SEQ ID NO 9
<211> LENGTH: 813
<212> TYPE: DNA
<213> ORGANISM: Rattus norvegicus

<400> SEQUENCE: 9
atggccaagc agggagaggc cgtcactcgc agaaccaagg tggctcccac caagaggatg      60
agcaggttct tgaagcactt cacagtggtg ggggacgact accacacctg gaatgtcaac     120
tacaagaagt gggagaacga ggaggatgag gaggagcccg ccccacgtc tgcggagggc     180 gagggcagtg ctgtgggccc agacgctgag gctggctctg cctccacacc caggccatcc     240
ctggacttca ggagccggct aaggaaactc ttcagttccc acaggtttca ggtcatcatc     300
atctgcctgg tggtcctgga cgccctcctg gtgctggctg agctccttct ggatttgagg     360
atcattgagc cggatctttc gaagtattcc acgaaggtat ccactatct gagtttagcc     420 atcctggcct tcttcgtgct ggagatctcc cttaaagtct ttgtcttccg cttggagttc     480
ttccaccaca gtttgagat cctggatgcc attgtggtgg tggtgtcctt tgtccttgac     540
ctcatcctcc tgtttaaaaa ccaccatttt gaagctcttg gtctgctgat ctgcttcgg     600 ctctggaggg tggcccggat catcaacggt atcatcatct cagtgaagac acgctctgaa     660
cggcagatct acggttaaa gcagataaac ctccaactgg ccaccaagat ccagcatctg     720
gaattcagct gctccgagaa ggaacaagaa attgagcgac tgagcaagct gttgagacag     780
aacggacttc ttgaggacgt gaacgtgaac taa                                  813
```

```
<210> SEQ ID NO 10
<211> LENGTH: 270
<212> TYPE: PRT
<213> ORGANISM: Rattus norvegicus

<400> SEQUENCE: 10

Met Ala Lys Gln Gly Glu Ala Val Thr Arg Arg Thr Lys Val Ala Pro
1               5                   10                  15

Thr Lys Arg Met Ser Arg Phe Leu Lys His Phe Thr Val Val Gly Asp
            20                  25                  30

Asp Tyr His Thr Trp Asn Val Asn Tyr Lys Lys Trp Glu Asn Glu Glu
        35                  40                  45
```

```
Asp Glu Glu Glu Pro Ala Pro Thr Ser Ala Glu Gly Glu Gly Ser Ala
        50                  55                  60

Val Gly Pro Asp Ala Glu Ala Gly Ser Ala Ser Thr Pro Arg Pro Ser
 65                  70                  75                  80

Leu Asp Phe Arg Ser Arg Leu Arg Lys Leu Phe Ser Ser His Arg Phe
                85                  90                  95

Gln Val Ile Ile Ile Cys Leu Val Val Leu Asp Ala Leu Leu Val Leu
                100                 105                 110

Ala Glu Leu Leu Leu Asp Leu Arg Ile Ile Glu Pro Asp Leu Ser Lys
            115                 120                 125

Tyr Ser Thr Lys Val Phe His Tyr Leu Ser Leu Ala Ile Leu Ala Phe
            130                 135                 140

Phe Val Leu Glu Ile Ser Leu Lys Val Phe Val Phe Arg Leu Glu Phe
145                 150                 155                 160

Phe His His Lys Phe Glu Ile Leu Asp Ala Ile Val Val Val Val Ser
                165                 170                 175

Phe Val Leu Asp Leu Ile Leu Leu Phe Lys Asn His His Phe Glu Ala
                180                 185                 190

Leu Gly Leu Leu Ile Leu Leu Arg Leu Trp Arg Val Ala Arg Ile Ile
            195                 200                 205

Asn Gly Ile Ile Ile Ser Val Lys Thr Arg Ser Glu Arg Gln Ile Leu
            210                 215                 220

Arg Leu Lys Gln Ile Asn Leu Gln Leu Ala Thr Lys Ile Gln His Leu
225                 230                 235                 240

Glu Phe Ser Cys Ser Glu Lys Glu Gln Glu Ile Glu Arg Leu Ser Lys
                245                 250                 255

Leu Leu Arg Gln Asn Gly Leu Leu Glu Asp Val Asn Val Asn
            260                 265                 270

<210> SEQ ID NO 11
<211> LENGTH: 810
<212> TYPE: DNA
<213> ORGANISM: Mus musculus

<400> SEQUENCE: 11
atgacttccc atgacccaaa ggccgtcact cgcagaacca aggtggctcc caccaagagg     60
atgagcaggt tcttgaaaca ctttacggtg gttgggacg actaccacac gtggaatgtc    120
aactacaaga gtgggagaa tgaggaggag gaggaggagc cagcgcccac atcagcagag    180
ggtgagggca tgctgagggg cccagatgcc gaggctggct ctgcctccac gcccaggcag    240
tccctggact tcaggagccg actgaggaaa ctcttcagtt cccacaggtt tcaggtcatc    300
atcatctgcc tggtggtcct ggacgccctc ctcgtgcttg ctgaactcct cctggatttg    360
aagatcatcg agccggacga gcaagactat gcggtcacgg cgttccacta catgagcttt    420
gccatcctgg tcttcttcat gttggagatt ttttttcaaga tcttcgtctt ccgcttagag    480
ttcttccacc acaagtttga gatcctggat gccttcgtgg tggtggtgtc tttcgtcctt    540
gaccttgtcc tcttgtttaa agccaccac ttcgaagctc tagggctgct gatcttgctt    600
cggctctgga gggtggcccg gatcatcaat ggcatcatca tctccgtgaa gacacgctca    660
gaacggcaga tcttaaggct aaagcagata aatatccaac tggccaccaa gatccagcat    720
ctggaattca gctgctccga aaggaacaa gaaattgagc ggctcaacaa gctgttgaaa    780
cagaatggac ttctcgggga cgtgaactag                                    810
```

<210> SEQ ID NO 12
<211> LENGTH: 269
<212> TYPE: PRT
<213> ORGANISM: Mus musculus

<400> SEQUENCE: 12

```
Met Thr Ser His Asp Pro Lys Ala Val Thr Arg Arg Thr Lys Val Ala
 1               5                  10                  15

Pro Thr Lys Arg Met Ser Arg Phe Leu Lys His Phe Thr Val Val Gly
            20                  25                  30

Asp Asp Tyr His Thr Trp Asn Val Asn Tyr Lys Lys Trp Glu Asn Glu
        35                  40                  45

Glu Glu Glu Glu Pro Ala Pro Thr Ser Ala Glu Gly Glu Gly Asn
    50                  55                  60

Ala Glu Gly Pro Asp Ala Glu Ala Gly Ser Ala Ser Thr Pro Arg Gln
65                  70                  75                  80

Ser Leu Asp Phe Arg Ser Arg Leu Arg Lys Leu Phe Ser Ser His Arg
                85                  90                  95

Phe Gln Val Ile Ile Ile Cys Leu Val Val Leu Asp Ala Leu Leu Val
            100                 105                 110

Leu Ala Glu Leu Leu Leu Asp Leu Lys Ile Ile Glu Pro Asp Glu Gln
        115                 120                 125

Asp Tyr Ala Val Thr Ala Phe His Tyr Met Ser Phe Ala Ile Leu Val
    130                 135                 140

Phe Phe Met Leu Glu Ile Phe Lys Ile Phe Val Phe Arg Leu Glu
145                 150                 155                 160

Phe Phe His His Lys Phe Glu Ile Leu Asp Ala Phe Val Val Val
                165                 170                 175

Ser Phe Val Leu Asp Leu Val Leu Leu Phe Lys Ser His His Phe Glu
            180                 185                 190

Ala Leu Gly Leu Leu Ile Leu Leu Arg Leu Trp Arg Val Ala Arg Ile
        195                 200                 205

Ile Asn Gly Ile Ile Ile Ser Val Lys Thr Arg Ser Glu Arg Gln Ile
    210                 215                 220

Leu Arg Leu Lys Gln Ile Asn Ile Gln Leu Ala Thr Lys Ile Gln His
225                 230                 235                 240

Leu Glu Phe Ser Cys Ser Glu Lys Glu Gln Glu Ile Glu Arg Leu Asn
                245                 250                 255

Lys Leu Leu Lys Gln Asn Gly Leu Leu Gly Asp Val Asn
            260                 265
```

<210> SEQ ID NO 13
<211> LENGTH: 708
<212> TYPE: DNA
<213> ORGANISM: Gallus gallus

<400> SEQUENCE: 13

```
atgtcccggt acctgaagca cttcacggtg gtgggggatg accccataca gtggagcaat    60
gattatcaga atgggagaa tgaggaggag gacaatggag agaaggactc ggagatcaaa    120 ctggagcect ccegtggcca cgtcaccttc aagatgtga tgaagaagct cttcagttca    180 cgcaggttte agattgtcat tgtcttcttg gtcatcgtgg atgccttgct ggtcctcggg    240
gaactgctga tggacttgaa gatcatccat ccggacaaat atcacatagc cccaaaggtt    300
ttccactacc tctccctttc cattctcacc atcttcctgg ttgaggtggg gtttaaaatc    360
```

```
tttgtttacg gccgggagtt cttccaccac aagtttgaag tgctggacag catcgttgtc    420
gtcgtgtcgt tcatccttga cctcgtcctc ctctttcggg agcatgagtt tgaagctgtg    480
gggctcctga ttctgctgcg gctgtggcgt gtggccagga tcatcaacgg aataatttta    540
tcggtgaaga ctcgctctga acaacaagtg tccaagctaa agcaggtgaa cctgaaactc    600
gcaacgaagg ttgaacaact tcaacacagc tgtgtggaga aggagcaaga aattgagagg    660
cttaccagga tgttaaaaca gcacgggctg ctcagcgagc aaacgtag               708
```

<210> SEQ ID NO 14
<211> LENGTH: 235
<212> TYPE: PRT
<213> ORGANISM: Gallus gallus

<400> SEQUENCE: 14

```
Met Ser Arg Tyr Leu Lys His Phe Thr Val Val Gly Asp Asp Pro Ile
 1               5                  10                  15

Gln Trp Ser Asn Asp Tyr Gln Lys Trp Glu Asn Glu Glu Glu Asp Asn
             20                  25                  30

Gly Glu Lys Asp Ser Glu Ile Lys Leu Glu Pro Ser Arg Gly His Val
         35                  40                  45

Thr Phe Gln Asp Val Met Lys Lys Leu Phe Ser Ser Arg Arg Phe Gln
     50                  55                  60

Ile Val Ile Val Phe Leu Val Ile Val Asp Ala Leu Leu Val Leu Gly
 65                  70                  75                  80

Glu Leu Leu Met Asp Leu Lys Ile Ile His Pro Asp Lys Tyr His Ile
                 85                  90                  95

Ala Pro Lys Val Phe His Tyr Leu Ser Leu Ser Ile Leu Thr Ile Phe
            100                 105                 110

Leu Val Glu Val Gly Phe Lys Ile Phe Val Tyr Gly Arg Glu Phe Phe
        115                 120                 125

His His Lys Phe Glu Val Leu Asp Ser Ile Val Val Val Ser Phe
    130                 135                 140

Ile Leu Asp Leu Val Leu Leu Phe Arg Glu His Glu Phe Glu Ala Val
145                 150                 155                 160

Gly Leu Leu Ile Leu Leu Arg Leu Trp Arg Val Ala Arg Ile Ile Asn
                165                 170                 175

Gly Ile Ile Leu Ser Val Lys Thr Arg Ser Glu Gln Gln Val Ser Lys
            180                 185                 190

Leu Lys Gln Val Asn Leu Lys Leu Ala Thr Lys Val Glu Gln Leu Gln
        195                 200                 205

His Ser Cys Val Glu Lys Glu Gln Glu Ile Glu Arg Leu Thr Arg Met
    210                 215                 220

Leu Lys Gln His Gly Leu Leu Ser Glu Gln Thr
225                 230                 235
```

<210> SEQ ID NO 15
<211> LENGTH: 693
<212> TYPE: DNA
<213> ORGANISM: Xenopus tropicalis

<400> SEQUENCE: 15

```
atggctgggt gtctgcgcca ttttacctct gtgggagatg acacaaaaaa aaaggcatgg     60
aaggaagaag atgtagaagt ggcacatgaa gaagaaccaa agaatactcc ccacccgttt    120
atagcctcat acagttttag gggagcccctt aaatggcttt ttagctccca caaatttcag    180
```

-continued

```
attgtgatta tttgccttgt aatcctcgat gcattatttg tgcttgtcga ggttcttctg    240
gatctggagc tgttagccga aaaagttgac cacattatac ctgagatatt tcactatctg    300
agcatttctg tcttgagctt ctttattttg gaaattgctg gtaaattgta tgccttccgc    360
cttgagttct tcatcacaa atttgaagtg tttgacgcag ccatcgttgt gatctccttt     420
atcattgaca ttgtctatat atctcgggaa gatatttcca atgccgtggg gctactgata    480
ctgcttcggc tttggagagt ggcaagaatt gtgaatggta taattgtgtc ggtcaagacc    540
caagcagagg ataagattca taggttgaaa gaaaaccaag agtcattgct tgagaaagtc    600
gcacacctgg agcagcagtg tgcccaacag gaacaagaga ttgtcagact tcagacgtta    660
ctgcagcagc acaatgtatt tcctgcttcc taa                                 693
```

<210> SEQ ID NO 16
<211> LENGTH: 230
<212> TYPE: PRT
<213> ORGANISM: Xenopus tropicalis

<400> SEQUENCE: 16

```
Met Ala Gly Cys Leu Arg His Phe Thr Ser Val Gly Asp Asp Thr Lys
 1               5                  10                  15

Lys Lys Ala Trp Lys Glu Glu Asp Val Glu Val Ala His Glu Glu
             20                  25                  30

Pro Lys Asn Thr Pro His Pro Phe Ile Ala Ser Tyr Ser Phe Arg Gly
         35                  40                  45

Ala Leu Lys Trp Leu Phe Ser Ser His Lys Phe Gln Ile Val Ile Ile
     50                  55                  60

Cys Leu Val Ile Leu Asp Ala Leu Phe Val Leu Val Glu Val Leu Leu
 65                  70                  75                  80

Asp Leu Glu Leu Leu Ala Glu Lys Val Asp His Ile Ile Pro Glu Ile
                 85                  90                  95

Phe His Tyr Leu Ser Ile Ser Val Leu Ser Phe Phe Ile Leu Glu Ile
                100                 105                 110

Ala Gly Lys Leu Tyr Ala Phe Arg Leu Glu Phe Phe His His Lys Phe
            115                 120                 125

Glu Val Phe Asp Ala Ala Ile Val Val Ile Ser Phe Ile Ile Asp Ile
        130                 135                 140

Val Tyr Ile Ser Arg Glu Asp Ile Phe Asn Ala Val Gly Leu Leu Ile
145                 150                 155                 160

Leu Leu Arg Leu Trp Arg Val Ala Arg Ile Val Asn Gly Ile Ile Val
                165                 170                 175

Ser Val Lys Thr Gln Ala Glu Asp Lys Ile His Arg Leu Lys Glu Asn
            180                 185                 190

Gln Glu Ser Leu Leu Glu Lys Val Ala His Leu Glu Gln Gln Cys Ala
        195                 200                 205

Gln Gln Glu Gln Glu Ile Val Arg Leu Gln Thr Leu Leu Gln Gln His
    210                 215                 220

Asn Val Phe Pro Ala Ser
225                 230
```

<210> SEQ ID NO 17
<211> LENGTH: 693
<212> TYPE: DNA
<213> ORGANISM: Xenopus laevis

<400> SEQUENCE: 17

```
atggctgggt gcctgcgcca tttacttct gtgggagatg acacaaaaaa aagggagtgg    60
aagcaagaag atgtagaagt ggcatatgaa gaaccactga agaatactcc ccatccattc   120
atagcctcgt acagttttag gggagcccct aaatggctat taagctccca caaatttcag   180
attgtgatta tttgccttgt aatcctcgac gcattatttg tacttgtcga ggttcttctg   240
gatctggagc tgttagctga aaaagttgac cacattatac ctgagatatt tcactatttg   300
agcatttctg tcttgacctt tttcattttg gaaattgctg gtaaattgta cgcttttcgc   360
cttgagttct ttcatcacaa gtttgaagta ttcgacgcag ctattgttgt gatctccttc   420
atcattgaca ttgtctatat ctctcgggaa gatattttca atgcggtcgg actactgata   480
ctgcttcggc tttggagagt tgcacgaatt gtgaatggtg taattgtgtc tgtgaagacc   540
cgagcagagg agaagatgca taagctgaaa gaacagaaag ggtcactgct tgagaaagtt   600
gcacaactgg agcagcaatg tgcccaacag gaacaagaga ttggcagact tcacaagtta   660
ctgcaggagc acaacgtatt tcctgcttcc taa                               693

<210> SEQ ID NO 18
<211> LENGTH: 230
<212> TYPE: PRT
<213> ORGANISM: Xenopus laevis

<400> SEQUENCE: 18

Met Ala Gly Cys Leu Arg His Phe Thr Ser Val Gly Asp Asp Thr Lys
  1               5                  10                  15

Lys Arg Glu Trp Lys Gln Glu Asp Val Glu Val Ala Tyr Glu Glu Pro
             20                  25                  30

Leu Lys Asn Thr Pro His Pro Phe Ile Ala Ser Tyr Ser Phe Arg Gly
         35                  40                  45

Ala Leu Lys Trp Leu Leu Ser Ser His Lys Phe Gln Ile Val Ile Ile
     50                  55                  60

Cys Leu Val Ile Leu Asp Ala Leu Phe Val Leu Val Glu Val Leu Leu
 65                  70                  75                  80

Asp Leu Glu Leu Leu Ala Glu Lys Val Asp His Ile Ile Pro Glu Ile
                 85                  90                  95

Phe His Tyr Leu Ser Ile Ser Val Leu Thr Phe Phe Ile Leu Glu Ile
            100                 105                 110

Ala Gly Lys Leu Tyr Ala Phe Arg Leu Glu Phe His His Lys Phe
            115                 120                 125

Glu Val Phe Asp Ala Ala Ile Val Val Ile Ser Phe Ile Ile Asp Ile
        130                 135                 140

Val Tyr Ile Ser Arg Glu Asp Ile Phe Asn Ala Val Gly Leu Leu Ile
145                 150                 155                 160

Leu Leu Arg Leu Trp Arg Val Ala Arg Ile Val Asn Gly Val Ile Val
                165                 170                 175

Ser Val Lys Thr Arg Ala Glu Glu Lys Met His Lys Leu Lys Glu Gln
            180                 185                 190

Lys Gly Ser Leu Leu Glu Lys Val Ala Gln Leu Glu Gln Gln Cys Ala
        195                 200                 205

Gln Gln Glu Gln Glu Ile Gly Arg Leu His Lys Leu Leu Gln Glu His
    210                 215                 220

Asn Val Phe Pro Ala Ser
225                 230

<210> SEQ ID NO 19
```

<211> LENGTH: 708
<212> TYPE: DNA
<213> ORGANISM: Danio rerio

<400> SEQUENCE: 19

```
atgtcccggt atctgaagca tttcaccgcg gtgggtgata taaaagcgc tgtcccaaca      60
tggcatgagg aagacacatc ccaccatgtc acgacattgc atgatgcccc tgatggcctg    120
gaggtttcaa caggacagca tttgggacag ctcagcttca gggactccct acgaaagctg    180
tacagtacag agagattcca gattgttgtt gtgtgcttgg ttgtcttgga tgccattttc    240
gtactatgcg agttgcttat tgacttgtct atcattgaag cagaccacca cagaatagcc    300
ccacaggtat tccactatct cagccttgcc cttctcacat tcttcatggt agagttggct    360
ggaaagatct ttgcctatcg cctagaattc cttcaccata gtttgaggt gtttgatggg     420
attgtggtgg tcgtatcctt tattttggat attatataca tctcaaaaga agatgcgttc    480
gatgccatgg gtctcctgat cttgctcagg ctctggagag tggccaggat cataaatggt    540
atcttggtgt ctgtgcaaaa tcgtgccaat acacagagttg aaaaactaaa ggagatcaac    600
gaaagcctcg ttcatcaagt caatgagctt aaagagcaga acacaaaaat ggaccaagaa    660
aacgtcaggc ttcgtgcgct cctaaaagat cacagcattg acttttaa                708
```

<210> SEQ ID NO 20
<211> LENGTH: 235
<212> TYPE: PRT
<213> ORGANISM: Danio rerio

<400> SEQUENCE: 20

```
Met Ser Arg Tyr Leu Lys His Phe Thr Ala Val Gly Asp Asn Lys Ser
  1               5                  10                  15

Ala Val Pro Thr Trp His Glu Glu Asp Thr Ser His His Val Thr Thr
             20                  25                  30

Leu His Asp Ala Pro Asp Gly Leu Glu Val Ser Thr Gly Gln His Leu
         35                  40                  45

Gly Gln Leu Ser Phe Arg Asp Ser Leu Arg Lys Leu Tyr Ser Thr Glu
     50                  55                  60

Arg Phe Gln Ile Val Val Val Cys Leu Val Val Leu Asp Ala Ile Phe
 65                  70                  75                  80

Val Leu Cys Glu Leu Leu Ile Asp Leu Ser Ile Ile Glu Ala Asp His
             85                  90                  95

His Arg Ile Ala Pro Gln Val Phe His Tyr Leu Ser Leu Ala Leu Leu
            100                 105                 110

Thr Phe Phe Met Val Glu Leu Ala Gly Lys Ile Phe Ala Tyr Arg Leu
        115                 120                 125

Glu Phe Leu His His Lys Phe Glu Val Phe Asp Gly Ile Val Val Val
    130                 135                 140

Val Ser Phe Ile Leu Asp Ile Ile Tyr Ile Ser Lys Glu Asp Ala Phe
145                 150                 155                 160

Asp Ala Met Gly Leu Leu Ile Leu Leu Arg Leu Trp Arg Val Ala Arg
                165                 170                 175

Ile Ile Asn Gly Ile Leu Val Ser Val Gln Asn Arg Ala Asn His Arg
            180                 185                 190

Val Glu Lys Leu Lys Glu Ile Asn Glu Ser Leu Val His Gln Val Asn
        195                 200                 205

Glu Leu Lys Glu Gln Asn Thr Lys Met Asp Gln Glu Asn Val Arg Leu
    210                 215                 220
```

```
Arg Ala Leu Leu Lys Asp His Ser Ile Asp Phe
225                 230                 235
```

<210> SEQ ID NO 21
<211> LENGTH: 600
<212> TYPE: DNA
<213> ORGANISM: Ciona intestinalis

<400> SEQUENCE: 21

```
atgtcatatt tatctataca ggttgcaatc atagtcctag tagtgttgga cagtttcctt      60
gtagttggtg aactccttat tgacctcaaa gtaatcattg taccacatgg taatcccgca     120
ccagagatat tacacgggtt ttctctctca attctatcaa tatttatggt ggaaatcgct     180
ttgaagataa tcgccgatca tcgtcacttc atacaccaca aggtggaagt gttggatgcg     240
gttgtcgtgg tgatatcgtt cggtgtcgat atcgctctta tattcgtcgg ggagagtgaa     300
gccctcgctg ctatcggact ccttgtcatt ctacggctgt ggagagtctt cagaatcatt     360
aatggtatca tcgtaacagt aaaaactaaa gcagacgata gagttcatga aataaagaaa     420
aagaattctg agctggaatt acaaattcat aatctagaag agaaactctc acaaaaggag     480
caagatatgt cccgcctgca tgagattcta cgttgcaata tatcgatat cccaccaaca      540
gtgcctttaa ctacttcagt gcaaatccat agtaccacaa cagcctctgc tgatgtttaa     600
```

<210> SEQ ID NO 22
<211> LENGTH: 199
<212> TYPE: PRT
<213> ORGANISM: Ciona intestinalis

<400> SEQUENCE: 22

```
Met Ser Tyr Leu Ser Ile Gln Val Ala Ile Ile Val Leu Val Val Leu
 1               5                  10                  15

Asp Ser Phe Leu Val Val Gly Glu Leu Leu Ile Asp Leu Lys Val Ile
             20                  25                  30

Ile Val Pro His Gly Asn Pro Ala Pro Glu Ile Leu His Gly Phe Ser
         35                  40                  45

Leu Ser Ile Leu Ser Ile Phe Met Val Glu Ile Ala Leu Lys Ile Ile
     50                  55                  60

Ala Asp His Arg His Phe Ile His His Lys Val Glu Val Leu Asp Ala
65                  70                  75                  80

Val Val Val Val Ile Ser Phe Gly Val Asp Ile Ala Leu Ile Phe Val
                 85                  90                  95

Gly Glu Ser Glu Ala Leu Ala Ala Ile Gly Leu Leu Val Ile Leu Arg
            100                 105                 110

Leu Trp Arg Val Phe Arg Ile Ile Asn Gly Ile Ile Val Thr Val Lys
        115                 120                 125

Thr Lys Ala Asp Asp Arg Val His Glu Ile Lys Lys Lys Asn Ser Glu
    130                 135                 140

Leu Glu Leu Gln Ile His Asn Leu Glu Glu Lys Leu Ser Gln Lys Glu
145                 150                 155                 160

Gln Asp Met Ser Arg Leu His Glu Ile Leu Arg Cys Asn Asn Ile Asp
                165                 170                 175

Ile Pro Pro Thr Val Pro Leu Thr Thr Ser Val Gln Ile His Ser Thr
            180                 185                 190

Thr Thr Ala Ser Ala Asp Val
        195
```

```
<210> SEQ ID NO 23
<211> LENGTH: 15
<212> TYPE: PRT
<213> ORGANISM: Artificial Sequence
<220> FEATURE:
<223> OTHER INFORMATION: Immunogenic Peptide based on mouse Hv1 protein

<400> SEQUENCE: 23

Cys Leu Asp Leu Lys Ile Ile Glu Pro Asp Glu Gln Asp Tyr Ala
1               5                   10                  15
```

METHODS OF USING VOLTAGE-GATED HV1 PROTON CHANNELS TO DETECT CHANGES IN INTRACELLULAR PH

RELATED APPLICATIONS

This application is a §371(c) national stage application of PCT/US2007/062253, filed Feb. 15, 2007, which claims the benefit of priority to U.S. Provisional Patent Appln. Ser. No. 60/773,398, filed Feb. 15, 2006 and to U.S. Provisional Patent Appln. Ser. No. 60/777,758, filed Mar. 1, 2006, the disclosures of which are incorporated by reference herein in their entireties.

BACKGROUND OF THE INVENTION

1. Field of the Invention

The present invention relates to the fields of molecular biology and drug discovery. In particular, the invention relates to a proton channel protein, nucleic acids encoding the protein, cells engineered to express the protein, assays for compounds affecting the activity of the protein, and the use of such compounds in the treatment of diseases and disorders.

2. Description of the Related Art

Voltage-dependent proton ($H^+$) conductances ($G_{vH}+$) were first discovered in molluscan neurons (Thomas et al. (1982), *Nature* 299: 826-8) and later identified in a variety of mammalian cell types such as: alveolar epithelial cells (DeCoursey (1991), *Biophys. J.* 60:1243-53), macrophages (Kapus et al. (1993) *J. Gen. Physiol.* 102:729-760), skeletal muscle (Krause et al. (1993), *Neuromuscul. Disord.* 3:407-11), osteoclasts (Nordstrom et al. (1995), *J. Biol. Chem.* 270: 2203-12), microglia (Eder and DeCoursey (2001), *Prog. Neurobiol.* 64:277-305), lymphocytes (Schilling et al. (2002) *J. Physiol.* 545:93-105), and others (reviewed in DeCoursey (2003), *Physiol. Rev.* 83:475-579). Indirect evidence suggests that $G_{vH}+$ are expressed in mammalian hippocampal neurons (Sheldon and Church (2002), *J. Neurophysiol.* 87:2209-24; Diarra et al. (1999), *Neuroscience* 93:1003-16). Among cells that have been tested, the highest density of voltage-dependent proton current is found in phagocytic leukocytes of the innate immune system (neutrophils and eosinophils) (DeCoursey (2003), supra).

Clearance of microbial, fungal and parasitic infections by phagocytes requires nicotinamide adenine dinucleotide phosphate (NADPH) oxidase activity, as evidenced by the development of chronic granulomatous disease (CGD) in humans and mice lacking functional gp91P$^{phox}$, the electron-transporting transmembrane subunit of the NADPH oxidase complex (Smith and Curnutte (1991), *Blood* 77:673-86). Activation of professional phagocytes (i.e. by bacterial peptides or complement) leads gp91$^{phox}$-dependent secretion of superoxide anion ($O_2.^-$) and concomitant generation of intracellular protons ($H^+$) and an outward electron ($e^-$) current (Henderson et al. (1987), *Biochem. J.* 246:325-9). Henderson and colleagues first postulated that a proton conductance could serve a charge-compensating role to limit intracellular acidification and thereby sustain $O_2.^-$ production (Henderson et al. (1987), supra); this hypothesis was extended and refined by DeCoursey and colleagues (DeCoursey (2003), *Physiol. Rev.* 83:475-579; Murphy and DeCoursey (2006), *Biochim. Biophys. Acta* 1757(8):996-1011).

The core biophysical features of $G_{vH}+$ elucidated using patch-clamp electrophysiology are: 1) Activation of $H^+$ conductance bye depolarizing (positive) voltage; 2) Sensitivity to the transmembrane $[H^+]$ (i.e. pH) gradient, which results in a shift of the threshold for voltage-dependent activation; 3) $H^+$-selective permeation (i. $Na^+$, $K^+$, and $Cl^-$ ions do not contribute to the measured current); 4) relatively slow activation kinetics (100's of msec time constants) and faster deactivation kinetics (tens of msec time constants)(DeCoursey (2003), supra). Under steady-state conditions in intact cells, these features dictate that $G_{vH}+$ are manifested as and outwardly-rectifying $H^+$ currents that result in net $H^+$ extrusion from cells and consequent intracellular alkalinization. The existence of a protein that would generate ionic currents with the properties of $G_{vH}+$ was long postulated but no cDNA sufficient to unambiguously reconstitute $G_{vH}+$ was reported until 2006 (Sasaki et al. (2006), *Science* 312:589-92; Ramsey et al. (2006), *Nature* 440:1213-6).

Voltage-dependent cation channels share an archetypal structure composed of two distinct domains: the VSD and the pore (P) domain (Long et al (2005a), *Science* 309(5736):897-903). The P domain is responsible for imparting cation-selective permeation whereas the VSD translates changes in the transmembrane electrical potential into protein conformational changes that lead to channel gating (Long et al. (2005b), *Science* 309(5736):903-8; Jiang et al. (2003), *Nature* 423:33-41).

SUMMARY OF THE INVENTION

The invention is based, in part, on the discovery of a novel voltage-gated proton-selective channel, designated Hv1, and uses therefor. Hv1 is expressed in immune tissue and manifests the characteristic properties of native proton conductances (GvH+) which are required in phagocytic leukocytes to support the respiratory burst that underlies microbial killing by the innate immune system. Thus, as detailed herein, the Hv1 channel is an attractive therapeutic target for the treatment of conditions in which the respiratory burst is implicated, as well as conditions in which proton-pumping or acid secretion is implicated. In addition, as detailed herein, the Hv1 channel and cells transformed to express the channel, are useful for screening and validating compounds that alter the activity of the Hv1 channel, as well as other ion channels.

In one aspect, the invention provides a method of identifying a potential modulator of Hv1 activity comprising: contacting a candidate compound with a cell expressing an Hv1 protein; measuring an indicator of Hv1 activity in the cell; determining whether the candidate compound caused an increase or decrease in the indicator relative to a reference level; and identifying the candidate compound as a potential modulator of Hv1 activity if the compound causes an increase or decrease in the indicator.

The indicator can be an indicator of the level of mRNA encoding the Hv1 protein, an indicator of the level of Hv1 protein, an indicator of proton flux across a membrane of the cell, an indicator of whole cell or channel currents of the cell, an indicator of whole cell or channel currents of the cell, an indicator of cellular pH. The indicator can be $Zn^{2+}$ sensitive.

In one embodiment, the cell has been transformed with a genetic construct which expresses an Hv1 protein. In another embodiment, the cell naturally expresses Hv1. In some embodiments, the cell is a COS cell or a HEK cell. The cell can be a cell having low native current.

In another aspect, the invention provides a method of identifying a potential modulator of Hv1 activity comprising: contacting under physiological conditions a candidate compound with an Hv1 moiety comprising at least a structural domain of an Hv1 protein; measuring binding, if any, between the candidate compound and the Hv1 moiety; and identifying the candidate compound as a potential modulator of Hv1 activity if the candidate compound binds to the Hv1 moiety.

In one embodiment, the Hv1 moiety is an Hv1 protein, a polypeptide having at least a transmembrane domain of an Hv1 protein or a polypeptide having at least an extracellular loop of an Hv1 protein.

In another aspect, the invention provides an isolated nucleic acid having a nucleotide sequence comprising a sequence selected from the group consisting of: (a) at least 10 consecutive nucleotides of SEQ ID NOs: 1, 3, 5, 7, 9, 11, 13, 15, 17, 19 or 21; (b) at least 12 consecutive nucleotides of SEQ ID NOs: 1, 3, 5, 7, 9, 11, 13, 15, 17, 19 or 21; (c) at least 14 consecutive nucleotides of SEQ ID NOs: 1, 3, 5, 7, 9, 11, 13, 15, 17, 19 or 21; (d) at least 16 consecutive nucleotides of SEQ ID NOs: 1, 3, 5, 7, 9, 11, 13, 15, 17, 19 or 21; (e) at least 18 consecutive nucleotides of SEQ ID NOs: 1, 3, 5, 7, 9, 11, 13, 15, 17, 19 or 21; (f) a sequence complementary to any one of the sequences of (a)-(e).

In yet another aspect the invention provides an isolated nucleic acid having a nucleotide sequence selected from the group consisting of: (a) a sequence encoding an Hv1 protein; (b) a sequence encoding at least a transmembrane domain of an Hv1 protein; (c) a sequence encoding at least an extracellular loop of an Hv1 protein; (d) a sequence encoding at least an epitope of an Hv1 protein having high predicted antigenicity; and (e) a sequence complementary to any one of the sequences of (a)-(d).

In one embodiment, the isolated nucleic acid is selected from the group consisting of: (a) a sequence encoding SEQ ID NOs: 2, 4, 6, 8, 10, 12, 14, 16, 18, 20 or 22; (b) a sequence encoding a polypeptide comprising residues 101-124, 137-163 or 138-158, 165-190 or 172-190, and 199-220 or 200-220 of SEQ ID NO: 2 or a non-human homolog thereof; (c) a sequence encoding a polypeptide comprising residues 125-137 or 126-136, 159-164 or 164-171, and 190-198 or 191-199 of SEQ ID NO: 2 or a non-human homolog thereof; (d) a sequence encoding a polypeptide comprising residues 1-100 of SEQ ID NO: 2 or a non-human homolog thereof; (e) a sequence encoding a polypeptide comprising residues 221-273 of SEQ ID NO: 2 or a non-human homolog thereof; (f) a sequence complementary to any one of the sequences of (a)-(e).

In one aspect, the invention provides an isolated nucleic acid encoding a polypeptide having at least 95% amino acid sequence identity with a polypeptide selected from the group consisting of: (a) an Hv1 protein; (b) at least a transmembrane domain of an Hv1 protein; (c) at least an extracellular loop of an Hv1 protein; and (d) an epitope of an Hv1 protein having high predicted antigenicity.

In another aspect, the invention provides an isolated nucleic acid encoding a polypeptide having at least 95% amino acid sequence identity with an Hv1 protein and having Hv1 activity in a cell capable of expressing Hv1 activity.

In still another aspect, the invention provides an isolated nucleic acid comprising a nucleotide sequence that hybridizes to a nucleic acid having a nucleotide sequence selected from the group consisting of SEQ ID NOs: 1, 3, 5, 7, 9, 11, 13, 15, 17, 19 and 21 under stringent conditions including a wash step of 1.0×SSC at 65° C., wherein the nucleic acid encodes a polypeptide having Hv1 activity.

In another aspect, the invention provides a nucleic acid comprising: (i) a nucleotide sequence encoding a polypeptide having Hv1 activity, wherein the nucleic acid hybridizes to a nucleic acid having a nucleotide sequence selected from the group consisting of SEQ ID NOs: 1, 3, 5, 7, 9, 11, 13, 15, 17, 19 and 21 under stringent conditions including a wash step of 1.0×SSC at 65° C.; and (ii) a heterologous regulatory region operably joined to the sequence such that the sequence is expressed.

In one aspect, the invention provides a nucleic acid comprising:

(i) a nucleotide sequence encoding a polypeptide having at least 95% amino acid sequence identity with a polypeptide having an amino acid sequence selected from the group consisting of SEQ ID NOs: 2, 4, 6, 8, 10, 12, 14, 16, 18, 20 and 22 and having Hv1 activity; and (ii) a heterologous regulatory region operably joined to the sequence such that the sequence is expressed.

In yet another aspect, the invention provides a kit for detecting at least a portion of an Hv1 nucleic acid comprising an isolated nucleic acid of the invention and a means for detecting the isolated nucleic acid. In one embodiment, the means for detecting the isolated nucleic acid comprises a detectable label bound thereto. In another embodiment, the means for detecting the isolated nucleic acid comprises a labeled secondary nucleic acid which specifically hybridizes to the isolated nucleic acid.

In one aspect, the invention provides a vector comprising an isolated nucleic acid described above. In one embodiment, the vector comprises a genetic construct which expresses a nucleic acid of the invention. In another embodiment, the nucleic acid is operably joined to an exogenous regulatory region. In yet another embodiment, the nucleic is operably joined to heterologous coding sequences to form a fusion vector.

In one aspect, the invention provides a cell transformed with a nucleic acid of the invention. In one embodiment, the cell is transformed with a genetic construct capable of expressing a nucleic acid of the invention. In one embodiment, the nucleic is operably joined to heterologous coding sequences to encode a fusion protein. In some embodiments, the cell is selected from the group consisting of bacterial cells, yeast cells, insect cells, nematode cells, amphibian cells, rodent cells, and human cells. In some embodiments, the cell is selected from the group consisting of mammalian somatic cells, fetal cells, embryonic stem cells, zygotes, gametes, germ line cells and transgenic animal cells.

In one aspect, the invention provides a non-human transgenic animal, wherein a genetic construct has introduced a modification into a genome of the animal, or an ancestor thereof, and wherein the modification is selected from the group consisting of insertion of a nucleic acid encoding at least a fragment of an Hv1 protein, inactivation of an endogenous Hv1 gene, and insertion by homologous recombination of a reporter gene operably joined to Hv1 regulatory elements.

In one embodiment, the modification is insertion of a nucleic acid encoding a polypeptide selected from the group consisting of an Hv1 protein, at least a transmembrane domain of an Hv1 protein, at least an extracellular loop of an Hv1 protein, at least a pore region of an Hv1 protein, and at least an epitope of an Hv1 protein having high predicted antigenicity.

The animal can be selected from the group consisting of rats, mice, hamsters, guinea pigs, rabbit, dogs, cats, goats, sheep, pigs, and non-human primates.

In another aspect, the invention provides a substantially pure protein preparation comprising a polypeptide selected from the group consisting of (a) an Hv1 protein; (b) at least a transmembrane domain of an Hv1 protein; (c) at least an extracellular loop of an Hv1 protein; (d) at least a pore region of an Hv1 protein; and (e) at least an epitope of an Hv1 protein having high predicted antigenicity.

In one embodiment, the polypeptide is selected from the group consisting of: (a) SEQ ID NO: 2 or a non-human homolog thereof; (b) residues 101-124, 137-163 or 138-158, 165-190 or 172-190, and 199-220 or 200-220 of SEQ ID NO: 2 or a non-human homolog thereof; (c) residues 125-137 or 126-136, 159-164 or 164-171, and 190-198 or 191-199 of SEQ ID NO: 2 or a non-human homolog thereof; (d) residues 1-100 of SEQ ID NO: 2 or a non-human homolog thereof; and (e) residues 221-273 of SEQ ID NO: 2 or a non-human homolog thereof.

In one aspect, the invention provides a substantially pure protein preparation comprising a polypeptide having at least 80% amino acid sequence identity with a polypeptide selected from the group consisting of: (a) an Hv1 protein; (b) at least a transmembrane domain of an Hv1 protein; and (c) at least an extracellular loop of an Hv1 protein.

In another aspect, the substantially pure protein preparation comprising a polypeptide having at least 80% amino acid sequence identity with an Hv1 protein and having Hv1 activity in a cell capable of expressing Hv1 activity.

In one aspect, the substantially pure antibody preparation comprises an antibody raised against an Hv1 epitope. In some embodiments, the epitope has high predicted antigenicity.

In one embodiment, the epitope comprises an amino acid sequence within the an amino acid sequence selected from the group consisting of approximately residues 1-29, 32-68, 78-100, 126-136, 191-199, 221-237 and 241-273 of SEQ ID NO: 2 an non-human homologs thereof. The antibody in the preparation can be a monoclonal antibody.

In one embodiment, the antibody is an antibody fragment selected from the group consisting of an Fab fragment, an F(ab')2 fragment, an Fv fragment, and a single-chain Fv fragment (scFv).

In one aspect, the invention provides a kit for detecting at least an epitope of an Hv1 protein comprising an anti-Hv1 antibody as described above and a means for detecting the antibody. In one embodiment, the means for detecting the anti-Hv1 antibody comprises a detectable label bound thereto. In another embodiment, the means for detecting the anti-Hv1 antibody comprises a labeled secondary antibody which specifically binds to the anti-Hv1 antibody.

In one aspect the invention provides a method of suppressing immune response in a subject comprising: administering to the subject a compound which decreases Hv1 activity.

In another aspect the invention provides a method of treating or preventing altitude sickness in a subject comprising: administering to the subject a compound which decreases Hv1 activity.

In yet another aspect the invention provides a method of treating inflammatory disease in a subject comprising: administering to the subject a compound which decreases Hv1 activity. The inflammatory disease can be rheumatoid arthritis.

In one aspect, the invention provides a method of treating chronic lung disease in a subject comprising: administering to the subject a compound which decreases Hv1 activity.

In another aspect, the invention provides a method of treating or preventing a cardiac reperfusion injury in a subject comprising: administering to the subject a compound which decreases Hv1 activity.

In one aspect, the invention provides a method of treating or preventing a neurodegenerative disease in a subject comprising: administering to the subject a compound which decreases Hv1 activity. The neurodegenerative disease can be Alzheimer's disease or amyotrophic lateral sclerosis.

In another aspect, the invention provides a method of treating chronic granulomatous disease in a subject comprising: administering to the subject a compound which increases Hv1 activity.

In one aspect, the invention provides a method of stimulating immune response in a subject who is an immune-compromised due to decreased superoxide production comprising: administering to the subject a compound which increases Hv1 activity.

In some embodiments, the compound is selected from the group consisting of a nucleic acid which is antisense to at least a portion of an Hv1 gene and an antibody to an Hv1 protein. In other embodiments, the compound is an antibody fragment selected from the group consisting of an Fab fragment, an F(ab')2 fragment, an Fv fragment, and an scFv fragment.

The subject can be a mammal, for example a human, a dog, a cat, a cow, a sheep, a horse, a mouse, a rat, a raccoon, or a gopher. The subject can be a fish, an amphibian or an insect.

In one aspect, the invention provides a method of diagnosing an Hv1-related disorder in a mammal comprising determining the presence or absence of a mutation in an Hv1 gene.

In one embodiment, the method comprises: determining at least a portion of an Hv1 gene sequence and comparing the determined sequence to a reference sequence; wherein the presence or absence of differences between the determined sequence and the reference sequence indicate the presence or absence of mutations in the Hv1 gene.

In another aspect, the invention provides a method of diagnosing an Hv1-related disorder comprising determining the presence or absence of a mutation in an Hv1 protein. In one embodiment, the method comprises: determining at least a portion of an Hv1 protein sequence and comparing the determined sequence to a reference sequence; wherein the presence or absence of differences between the determined sequence and the reference sequence indicate the presence or absence of mutations in the Hv1 gene.

In one embodiment, the determination comprises contacting at least a fragment of the Hv1 protein with an antibody known to bind to an Hv1 protein in which a mutation is known to be present or absent and detecting binding between the antibody and the fragment of the Hv1 protein.

In one aspect, the invention provides a method of diagnosing an Hv1-related disorder in a mammal comprising: measuring an indicator of Hv1 activity in the cell; comparing the measured indicator to a reference level; and diagnosing an Hv1-related disorder if the indicator increases or decreases.

The indicator can be an indicator of the level of mRNA encoding the Hv1 protein, an indicator of the level of Hv1 protein, an indicator of proton flux across a membrane of the cell, an indicator of whole cell or channel currents of the cell.

In some embodiments, the disorder is selected from the group consisting of an immune disorder, altitude sickness, an inflammatory disease or disorder, a reperfusion injury, chronic granulomatous disease and a chronic lung disease.

In one aspect, the invention provides a method of genotyping a subject with respect to an Hv1 gene comprising: determining at least a portion of an Hv1 gene sequence and comparing the determined sequence to a reference sequence; wherein the presence or absence of differences between the determined sequence and the reference sequence indicate the presence or absence of a genotype corresponding to the reference sequence.

In another aspect, the invention provides a method of genotyping a subject with respect to an Hv1 gene comprising: determining at least a portion of an Hv1 protein sequence and comparing the determined sequence to a reference sequence; wherein the presence or absence of differences between the determined sequence and the reference sequence indicate the presence or absence of a genotype corresponding to the reference sequence. The determination can comprise contacting at least a fragment of the Hv1 protein with an antibody known to bind to an Hv1 protein comprising the reference sequence and detecting binding between the antibody and the fragment of the Hv1 protein.

In one aspect, the invention provides a method of detecting activity of a non-electrogenic biomolecule comprising: obtaining a cell transformed with an exogenous genetic construct whereby the cell expresses an Hv1 protein having Hv1 activity; varying an intracellular or extracellular condition which affects a non-electrogenic activity of the non-electrogenic biomolecule, whereby the non-electrogenic activity causes a change in intracellular pH; detecting a change in an electrical signal caused by the Hv1 protein in response to the change in intracellular pH, whereby the activity of the non-electrogenic biomolecule is detected.

BRIEF DESCRIPTION OF THE DRAWINGS

The following drawings are illustrative of certain embodiments of the invention but is not meant to limit the scope of the invention.

FIG. 2 is an amino acid sequence alignment a human Hv1protein and ten non-human Hv1homologs from *Macaca mulatta* (SEQ ID NO: 4), *Bos taurus* (SEQ ID NO: 6), *Canis familiaris* (SEQ ID NO: 8), *Rattus norvegicus* (SEQ ID NO: 10), *Mus musculus* (SEQ ID NO: 12), *Gallus gallus* (SEQ ID NO: 14), *Xenopus tropicalis* (SEQ ID NO: 16), *Xenopus laevis* (SEQ ID NO: 18), *Danio rerio* (SEQ ID NO: 20), and *Ciona intestinalis* (SEQ ID NO: 21). Putatitive transmembrane segments, identified by a second method, are shown in boxes.

FIG. 3 shows the alteration of current flow of the GFP-hHv1 G199C mutant by 2-(trimethylammonium)methanethiosulfonate;

FIG. 4 shows a schematic overview of HVCN1 genetrap;

DETAILED DESCRIPTION

Figure 1:
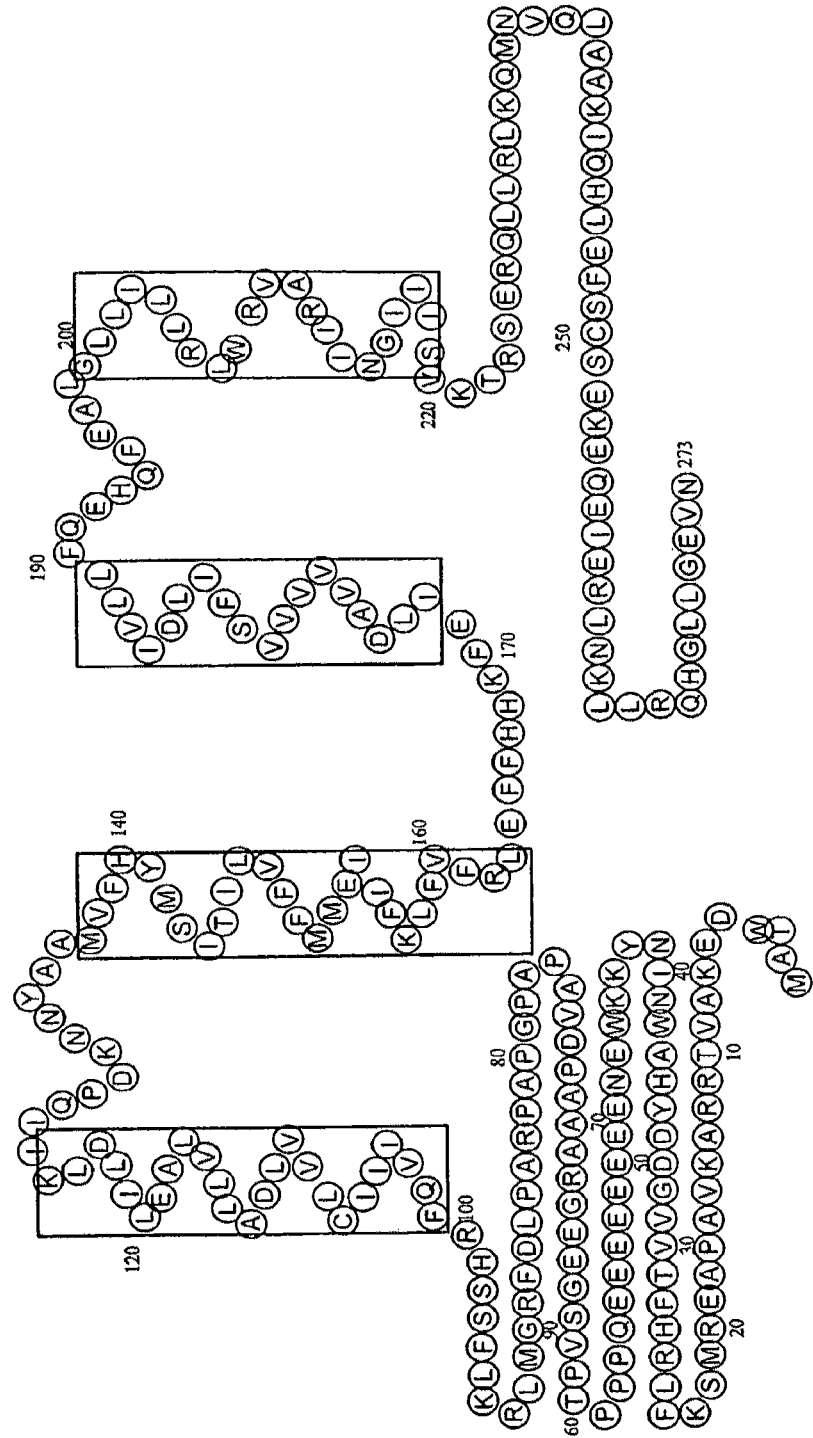
FIG. 1 is a schematic diagram of a human Hv1protein (SEQ ID NO: 2) with putatitive transmembrane segments, identified by a first method, shown in boxes.

The present invention depends, in part, upon the identification, isolation and characterization of a novel voltage-gated proton channel, designated Hv1, which involved in the respiratory burst phase in phagocytic killing of microbial by providing a proton pump needed to counterbalance the depolarizing electron current generated by NADPH oxidase. The channel has been designated Hv1 to indicate that it is a voltage-gated $H^+$ channel protein. The Hv1 channel contains four predicted transmembrane domains, but does not appear to contain a pore domain. The mRNA is enriched in immune tissues such as lymph node, B-lymphocytes, monocytes and spleen. Hv1, therefore, represents an attractive target for the screening and design of agonists and antagonists of the respiratory burst phase in leukocytes, which may serve as drugs for a number of indications, including those related to inflammation and acid secretion. The protein has also been shown to be expressed in hippocampal neurons, respiratory epithelium and other tissues.

References and Definitions

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference.

All technical and scientific terms used herein, unless otherwise defined below, are intended to have the same meaning as commonly understood by one of ordinary skill in the art; and references to techniques employed herein are intended to refer to the techniques as commonly understood in the art, including variations on those techniques or substitutions of equivalent techniques which would be apparent to one of skill in the art. In order to more clearly and concisely describe the subject matter which is the invention, the following definitions are provided for certain terms which are used in the specification.

As used herein, the term "Hv1 protein" means the human Hv1 protein disclosed in SEQ ID NO: 2 and naturally-occurring allelic variants thereof, non-human homologs of these human Hv1 proteins (e.g., SEQ ID NOs: 4, 6, 8, 10, 12, 14, 16, 18, 20 and 22), and naturally-occurring allelic variants thereof; and functional equivalents thereof. The term Hv1 protein includes naturally occurring Hv1 proteins as isolated from cells expressing the protein, recombinantly produced Hv1 proteins from cells transformed with Hv1 genes, and fusion proteins in which Hv1 sequences are fused to N-terminal or C-terminal polypeptides. The term "Hv1 fragment" refers to a fragment of at least six amino acid residues of an Hv1 protein, including but not limited to the structural domains and epitopes described herein.

As used herein, the term "Hv1 gene" means a gene encoding a Hv1 protein. The term Hv1 gene refers to both naturally occurring genes as isolated from genomic DNA, and recombinantly produced genes in which the Hv1 coding regions are operably joined to either endogenous or exogenous regulatory elements, with or without intron sequences, and with or without 5' or 3'-flanking sequences which can encode heterologous (i.e., non-Hv1) sequences to form a Hv1 fusion protein. An Hv1 gene will include, at a minimum, a coding region encoding the protein operably joined to regulatory elements (e.g., promoter, enhancer) which allow transcription of the coding region to mRNA which can be translated into a Hv1 protein.

As used herein "Hv1" activity means any normal biological activity of a wild-type Hv1 protein when expressed in a cell or cell type in which Hv1 is normally expressed and under conditions under which Hv1 is normally expressed. Such activity can include induction of a proton current, or counterbalancing the depolarizing electron current generated by NADPH oxidase. Hv1 activity can be measured in cells in which Hv1 is naturally-occurring (e.g., leukocytes), or in cells which have been transformed with an exogenous construct to cause Hv1 expression (e.g., transformed HEK, COS cells).

As used herein with respect to nucleic acid and amino acid sequences, the term "identity" means a measure of the degree of similarity of two sequences based upon an alignment of the sequences which maximizes identity and which is a function of the number of identical nucleotides or residues in the aligned sequences, the number of total nucleotides or residues, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (the NCBI website), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:3389-3402); Zhang et al. (2000), *J. Comput. Biol.* 7(1-2):203-14. As used herein, percent similarity of two amino acid sequences is the score based upon the following parameters for the BLASTp algorithm: word size =3; gap opening penalty =−11; gap extension penalty =−1; and scoring matrix =BLOSUM62. As used herein, percent similarity of two nucleic acid sequences is the score based upon the following parameters for the BLASTn algorithm: word size =11; gap opening penalty =−5; gap extension penalty =−2; match reward =1; and mismatch penalty =−3.

As used herein, the term "homolog" means a protein which is evolutionarily-related to and shares substantial, conserved structural and functional similarity with a reference protein, but which is naturally present in a different species (e.g., the Hv1 proteins of SEQ ID NO: 1, 3, 5, 7, 9, 11, 13, 15, 17, 19 and 21 are homologs of each other).

As used herein, the term "mutation" refers to a change in an amino acid sequence relative to some reference sequence. The reference sequence can be a "wild-type" sequence (i.e., one or more sequences in a population corresponding to a "normal" phenotype), or any other sequence. As used herein, the term mutation is intended to be synonymous with the term polymorphism, and therefore the differences between any two non-identical sequences can be regarded as mutations. The term mutation is intended to encompass insertions, deletions and/or substitutions of one or more amino acids relative to a reference sequence. As used herein, the term "mutant" refers to a protein including a mutation, or an organism expressing a mutation.

As used herein, the terms "exogenous" and "heterologous" mean, with respect to two or more genetic sequences, that the genetic sequences do not occur in the same physical relation to each other in nature and/or do not naturally occur within the same genome. For example, a genetic construct can include a coding region which is operably joined to one or more regulatory elements, and these sequences are considered heterologous to each other if they are not operably joined in nature and/or they are not found in the same genome in nature. Similarly, a genetic construct which is introduced into a cell is considered heterologous to that cell to the extent that it contains genetic sequences not found in that cell. In addition, a synthetically-produced genetic sequence based upon a naturally occurring sequence, will be heterologous to the naturally-occurring sequence to the extent the sequence has been altered and the synthetic sequence does not exist in nature. Allelic variants of a sequence in a species are not considered heterologous to each other.

As used herein, the term "operably joined" refers to a covalent and functional linkage of genetic regulatory elements and a genetic coding region which can cause the coding region to be transcribed into mRNA by an RNA polymerase which can bind to one or more of the regulatory elements. Thus, a regulatory region, including regulatory elements, is operably joined to a coding region when RNA polymerase is capable under permissive conditions of binding to a promoter within the regulatory region and causing transcription of the coding region into mRNA. In this context, permissive conditions would include standard intracellular conditions for constitutive promoters, standard conditions and the absence of a repressor or the presence of an inducer for repressible/inducible promoters, and appropriate in vitro conditions, as known in the art, for in vitro transcription systems.

As used herein, the term "expression" refers to the process by which a coding sequence of a gene is transcribed into a primary mRNA transcript, the primary mRNA transcript is processed into a mature mRNA, and the mature mRNA is translated into a protein. Expression can optionally include post-translation modifications of the resulting polypeptide.

As used herein, the phrase "genetic construct encoding an Hv1 protein" means a recombinant DNA, RNA, DNA-RNA hybrid, or nucleic acid analog molecule which includes a genetic sequence encoding, or which is complementary to a genetic sequence encoding, the amino acid sequence of the Hv1 protein, and which is capable of being expressed in a cell which has been transformed with the construct. The construct can express the Hv1 protein transiently, or can stably integrate into the genome of the cell and express the protein conditionally or constitutively.

As used herein, the term "vector" means any genetic construct, such as a plasmid, phage, transposon, cosmid, chromosome, virus, virion, etc., which is capable of transferring gene sequences between cells. Vectors are capable of one or more of replication, expression, and insertion or integration, but need not possess each of these capabilities. Thus, the term includes cloning, expression, homologous recombination, and knock-out vectors.

As used herein, with respect to genetic engineering, the term "transform" means to introduce into a cell or an organism an exogenous nucleic acid or nucleic acid analog which replicates within that cell or organism, that encodes a polypeptide sequence which is expressed in that cell or organism, and/or that is integrated into the genome of that cell or organism so as to cause the expression of a polypeptide. The term "transform" is used to embrace all of the various methods of introducing such nucleic acids or nucleic acid analogs, including, but not limited to the methods referred to in the art as transformation, transfection, transduction, electroporation, ballistic injection, and the like.

As used herein, a "nucleic acid analog" means a molecule having sufficient structural and functional similarity to a nucleic acid to direct sequence-specific forward or reverse transcription of complementary nucleic acids, or to direct sequence-specific translation of an encoded polypeptide within a living cell or in vitro translation system. As used herein, whenever the term "nucleic acids" is used, the term is intended to embrace nucleic acid analogs when such analogs would be useful or suitable in the context of the usage.

As used herein, the term "reporter gene" means any genetic sequence which, when expressed, has a biochemical or phenotypic effect which is detectable. Reporter genes are also known in the art as "marker" genes.

As used herein, the term "antibody" is intended to embrace naturally produced antibodies, recombinantly produced antibodies, and antibody fragments such as Fab fragments, F(ab')$_2$ fragments, Fv fragments, and single-chain Fv fragment (scFv).

As used herein, the term "effective amount" of an agonist or antagonist, or an enhancer or repressor, means the total amount of the active component(s) of a composition that is sufficient to cause a statistically significant change of a detectable biochemical or phenotypic characteristic. When applied to an individual active ingredient, administered alone, the term refers to that ingredient alone. When applied to a combination, the term refers to combined amounts of the active ingredients that result in the effect, whether administered in combination, serially or simultaneously.

As used herein, the term "substantially pure" means a preparation which contains at least 60% (by dry weight) of the protein of interest, exclusive of the weight of other intentionally included compounds. In certain embodiments, the preparation is at least 75%, at least 90%, or at least 99% the protein of interest by dry weight, exclusive of the weight of other intentionally included compounds. Purity can be measured by any appropriate method (e.g., column chromatography, gel electrophoresis, amino acid compositional analysis or HPLC analysis). If a preparation intentionally includes two or more different proteins of the invention, a "substantially pure" preparation means a preparation in which the total dry weight of the proteins of the invention is at least 60% of the total dry weight, exclusive of the weight of other intentionally included compounds. For preparations containing two or more proteins of the invention, the total weight of the proteins of the invention should be at least 75%, at least 90%, or at least 99%, of the total dry weight of the preparation, exclusive of the weight of other intentionally included compounds. Thus, if the proteins of the invention are mixed with one or more other compounds (e.g., diluents, stabilizers, detergents, excipients, salts, sugars, lipids) for purposes of administration, stability, storage, and the like, the weight of such other compounds is ignored in the calculation of the purity of the preparation.

As used herein, the terms "modulate" or "affect" mean to either increase or decrease. As used herein, the terms "increase" and "decrease" mean, respectively, statistically significantly increase (i.e., $p<0.1$) and statistically significantly decrease (i.e., $p<0.1$).

As used herein, the term "contacted" as in the phrase "A is contacted with B," means that A and B are brought into sufficient physical proximity to interact at the molecular level, as by mixing A and B together in a solution, or pouring a solution of A over B on a substrate. As used herein, the phrase "A is contacted with B" is intended to be equivalent to "B is contacted with A" and is not intended to imply that either element is fixed relative to the other, or that either element is moved relative to the other.

As used herein, the recitation of a numerical range for a variable is intended to convey that the invention may be practiced with the variable equal to any of the values within that range. Thus, for a variable which is inherently discrete, the variable can equal each integer value of the numerical range, including the end-points of the range. Similarly, for a variable which is inherently continuous, the variable can equal each real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value≤2 for variables which are inherently continuous.

As used herein, unless specifically indicated otherwise, the word "or" is used in the "inclusive" sense of "and/or" and not the "exclusive" sense of "either/or."

General Considerations

The present invention depends, in part, upon the identification, isolation and characterization of a novel voltage-gated proton channel protein, designated Hv1, which is expressed in immune tissues including lymph node, B-lymphocytes, monocytes and spleen, and which plays a significant role in the respiratory burst phase in leukocytes. Therefore, compounds which increase or decrease the activity of the Hv1 protein can be used to treat or prevent conditions in which insufficient or excessive respiratory burst activity is implicated. Moreover, because the Hv1 channel protein functions to transport protons across the cell membrane, compounds which increase or decrease the activity of the Hv1 protein can be used to treat or prevent conditions in which insufficient or excessive proton pump activity is implicated.

The Hv1 channel is in the family of a voltage sensor domain (VSD) proteins, and has homology to the first four transmembrane segments (S1-S4) of known voltage-dependent cation channels (i.e., $K_v$, $Na_v$, $Ca_v$) (see, Long et al. (2005a), supra). The protein has also been described by Sasaki et al. (2006), supra, as the voltage-sensor domain only protein (VSOP).

The predicted human Hv1 protein is 273 amino acids in length, with a predicted molecular weight of 31.7 kDa, and an isoelectric point (pI) of 6.62. The Hv1 protein forms four transmembrane segments (S1-S4), according to hydropathy analyses, and both the amino-terminus and carboxy-terminus are believed to be on the cytoplasmic side of the cell membrane (see FIG. 1). The overall transmembrane (TM) structure and placement of charged residues in the hydrophobic domains is conserved among the vertebrate Hv1 orthologues and similar to both the Ci-VSP protein of the sea squirt *Ciona instestinalis* (Murata et al. (2005), *Nature* 435: 1239-1243; FIG. 2, SEQ ID NO: 11) and the voltage-sensing domain (VSD) of $K_v$ 1.2 (Long et al. (2005a)). The amino-terminal ~100 amino acids in Hv1 are homologous to protein and lipid phosphatases, but unlike the catalytically active Ci-VSP, the core active site residues required for phosphatase activity are not conserved in Hv1. Like other members of the family, the Hv1 channel is $Zn^{++}$ sensitive.

A sequence alignment of the predicted amino acid sequences of a number of vertebrate species and the chordate *Ciona intestinalis* is shown in FIG. 2. Specifically, FIG. 2 shows the predicted complete amino acid sequences of the human (*Homo sapiens*) homolog (SEQ ID NO: 2), rhesus monkey (*Macaca mulatta*) homolog (SEQ ID NO: 4), cow (*Bos taurus*) homolog (SEQ ID NO: 6), dog (*Canis familiaris*) homolog (SEQ ID NO: 8), rat (*Rattus norvegicus*) homolog (SEQ ID NO: 10), mouse (*Mus musculus*) homolog (SEQ ID NO: 12), chicken (*Gallus gallus*) homolog (SEQ ID NO: 14), pipid frog (*Xenopus tropicallis*) homolog (SEQ ID NO: 16), African Clawed Frog (*Xenopus laevis*) homolog (SEQ ID NO: 18), zebrafish (*Danio rerio*) homolog (SEQ ID NO: 20), and sea squirt (*Ciona intestinalis*) homolog (SEQ ID NO: 22).

Significantly, the predicted transmembrane regions S1-S4 (shown in boxes) of the voltage-sensing domains of these different Hv1 species homologs shows substantial similarities. The residue numbering represents the linear amino acid positions in human Hv1 homolog.

Hv1 Nucleic Acids

In one aspect, the present invention provides nucleic acid molecules, or nucleic acid analogs, encoding the Hv1 proteins, or useful fragments thereof. One cDNA of a human Hv1 gene has been identified and is disclosed as SEQ ID NO: 1, and as Genbank Accession No. BC032672. Full-length cDNA sequences of a rhesus monkey (*Macaca mulatta*) homolog are disclosed as SEQ ID NO: 3 and as Genbank Accession Nos. XM 001107933, XM 001107990, XM 001108044 and XM 001108107; a cow (*Bos taurus*) homolog is disclosed as SEQ ID NO: 5 and as Genbank Accession No. XM 868620; a dog (*Canis familiaris*) homolog is disclosed as SEQ ID NO: 7 and as Genbank Accession No. XM 856580; a rat (*Rattus norvegicus*) homolog is disclosed as SEQ ID NO: 9 and as Genbank Accession No. XM 001079575; a mouse (*Mus musculus*) homolog is disclosed as SEQ ID NO: 11 and as Genbank Accession Nos. NM 001042489 and NM 028752; a chicken (*Gallus gallus*) homolog is disclosed as SEQ ID NO: 13 and as Genbank Accession No. NM 001030663; a pipid frog (*Xenopus tropicallis*) homolog is disclosed as SEQ ID NO: 15 and as Genbank Accession No. NM 001011262; an African Clawed Frog (*Xenopus laevis*) homolog is disclosed as SEQ ID NO: 17 and as Genbank Accession No. BC 088681; a zebrafish (*Danio rerio*) homolog is disclosed as SEQ ID NO: 19 and as Genbank Accession No. BC075916;

and a sea squirt (*Ciona intestinalis*) homolog is disclosed as SEQ ID NO: 21 and as Genbank Accession No. CI 0100130706.

Nucleic acid molecules of the invention can be DNA or RNA molecules, or hybrid DNA-RNA molecules. The nucleic acid analogs of the invention can be any of those known in the art, such as peptide nucleic acids, analogs including modified bases (e.g., 2'-halo-2'-deoxynucleotides) and/or analogs including modified internucleoside linkages (e.g., phosphorothioate linkages), which are useful in applications such as in vitro translation or antisense technologies. The nucleic acids can be sense molecules corresponding to all or a portion of an Hv1 gene sequence, or can be antisense molecules which are complementary to all or a portion of an Hv1 gene sequence. The nucleic acids can be derived from or correspond to genomic DNA or cDNA, or can be synthetic molecules based upon an Hv1 protein sequence and the genetic code (e.g., synthetic nucleic acids which reflect the codon usage preferences in the host cells used in an expression system).

In some embodiments, the Hv1 nucleic acids comprise the entire coding region of an Hv1 gene (e.g., SEQ ID NO: 1). Such nucleic acids can be used to produce genetic constructs for transformation of cells, or for in vitro transcription and translation systems. Such nucleic acids can also be used as probes in hybridization assays to detect Hv1 Sequences in samples of other nucleic acids.

In other embodiments, subsets of the Hv1 nucleic acid sequences are provided for use as primers for nucleic acid amplification reactions, as probes in hybridization assays to detect Hv1 sequences in samples of other nucleic acids, or as probes to distinguish normal or wild-type sequences from abnormal or mutant sequences. In these embodiments, the nucleic acids of the'invention comprise at least 10, 12, 14, 16 or 18 consecutive nucleotides selected from a Hv1 sequence such as any one of SEQ ID NOs: 1, 3, 5, 7, 9, 11, 13, 15, 17, 19 and 21. Depending upon the nature of the application, it can be preferable to choose Hv1 sequences which will have unique targets, or which are expected to have unique targets, within a sample being probed or amplified. Thus, for example, sequences which are longer and sequences which do not include frequently repeated elements (for example, polyadenylation signals) are more likely to be uniquely represented within any given sample. For purposes of choosing primers for amplification reactions, sequences of at least 15 nucleotides, and typically 18-25 nucleotides, are used.

In certain embodiments, nucleic acids are provided which encode structural domains of an Hv1 protein, or which encode fragments of the protein which can serve as epitopes for the generation of antibodies. Thus, for example, useful nucleic acids include those encoding the transmembrane domains of the Hv1 proteins identified in FIG. 2 (e.g., approximately residues 101-124, 137-163 or 138-158, 165-190 or 172-190, and 199-220 or 200-220 of SEQ ID NO: 2, and allelic variants and homologs thereof), encoding the extracellular loops between transmembrane domains (e.g., approximately residues 125-137 or 126-136, 159-164 or 164-171, and 190-198 or 191-199 of SEQ ID NO: 2, and allelic variants and homologs thereof. Other useful nucleic acids include those encoding potential epitopes of the Hv1 proteins, as identified by standard sequence analysis techniques described below. Thus, for example, useful nucleic acids can include those encoding the following human Hv1 sequences: residues 1-29, 32-68, 78-100, 126-136, 191-199, 221-237 and residues 241-273 of SEQ ID NO: 2. Other useful epitopes include allelic and non-human mammalian homologs of these epitopes.

In certain embodiments, nucleic acids are provided which encode polypeptides have at least 80%, 85%, 90% or 95% amino acid sequence identity with at least a structural domain of an Hv1 protein. Thus, in some embodiments, a nucleic acid is provided which encodes a polypeptide having at least 80%, 85%, 90% or 95% amino acid sequence identity with a transmembrane domain of an Hv1 protein (e.g., approximately residues 101-124, 137-163 or 138-158, 165-190 or 172-190, and 199-220 or 200-220 of SEQ ID NO: 2; and allelic variants and homologs thereof), an extracellular loop between transmembrane domains (e.g., approximately residues 125-137 or 126-136, 159-164 or 164-171, and 190-198 or 191-199 of SEQ ID NO: 2; and allelic variants and homologs thereof. In some embodiments, nucleic acids are provided encoding a polypeptide having at least 80%, 85%, 90% or 95% amino acid sequence identity with an Hv1 protein and having Hv1 activity. The ability of a protein to exhibit Hv1 activity can be measured by its ability to complement an Hv1−/−mutant (e.g., a Hv1 knock-out mutant) and restore a normal or Hv1+/+phenotype (e.g., to restore whole-cell current) in a cell otherwise capable of expressing Hv1 activity (e.g., an immune tissue cell from an Hv1−/− mutant or knock-out).

In other embodiments, isolated nucleic acids are provided which include a nucleotide sequence that hybridizes to at least a portion of an Hv1 coding sequence (e.g., SEQ ID NO: 1) under stringent hybridization conditions. Such conditions include hybridizations employing a wash step of 1.0×SSC at 65° C., and equivalents thereof. More stringent conditions can include wash steps of 0.5×SSC, 0.2×SSC, or even 0.1× SSC. Other equivalently stringent conditions are well known in the art. See, e.g., Ausubel et al., eds. (1989), *Current Protocols in Molecular Biology*, Vol. I, John Wiley & Sons, Inc., New York. In some embodiments, the nucleic acid encodes a polypeptide having Hv1 activity.

In another aspect, the invention provides nucleic acids, either isolated or existing within cells, in which a nucleotide sequence encoding a polypeptide having Hv1 activity is operably joined to a heterologous regulatory region such that the Hv1 sequence is expressed. Thus, in certain embodiments, a heterologous regulatory region can be inserted into a chromosome such that it is operably joined to an endogenous Hv1 sequence. In other embodiments, an exogenous sequence encoding an Hv1 polypeptide can be inserted into a chromosome such that it is operably joined to a heterologous regulatory region. In yet other embodiments, an exogenous genetic construct including a sequence encoding an Hv1 polypeptide operably joined to a regulatory region (whether heterologous or not) is inserted into a chromosome. In any of such embodiments, the Hv1 polypeptide can have at least 80%, 85%, 90% or 95% amino acid sequence identity with an amino acid sequence of at least one of SEQ ID NOs: 2, 4, 6, 8, 10, 12, 14, 16, 18, 20 and 22. In other embodiments, the nucleic acid encoding the polypeptide hybridizes to at least a portion of a nucleic acid of at least one of SEQ ID NO: 1, 3, 5, 7, 9, 11, 13, 15, 17, 19 and 21 under conditions including a wash step of 1.0×SSC at 65° C., 0.5×SSC, 0.2×SSC, or 0.1× SSC.

In certain embodiments, the nucleic acids of the invention encode polypeptides including a Hv1 sequence of at least 50 amino acid residues in length, or at least 100, 200 or 300 amino acid residues in length. These polypeptides can include a Hv1 sequence which includes at least one transmembrane domain, at least one extracellular loop domain, or combinations thereof. In some embodiments, the polypeptide has Hv1 activity. Such activity can include induction of proton current; mediation of hydrogen peroxide generation; and restoration of proton flux.

In another aspect, the invention provides kits for detecting at least a portion of an Hv1 nucleic acid (e.g., Hv1 genomic DNA, mRNA, cDNA or amplification products thereof). The kits include an isolated nucleic acid of the invention as a probe and means for detecting the probe. The means for detecting the probe can be a detectable label bound to the probe or a secondary nucleic acid probe for detecting the first probe (e.g., labeled secondary nucleic acid which specifically hybridizes to the isolated nucleic acid).

Genetic Constructs

In another aspect, the present invention provides genetic constructs comprising sequences selected from Hv1 genes. In certain embodiments, the Hv1 gene sequences are selected from the coding region of the Hv1 gene, and in other embodiments, the Hv1 gene sequences can be chosen from the Hv1 regulatory regions extending approximately 1,000 bases 5' of the transcription initiation codon, and extending approximately 1,000 bases 3' of the termination codon.

In one series of embodiments, Hv1 coding sequences (e.g., the entire coding region, sequences encoding structural domains, sequences encoding potential epitopes, or sequences encoding useful primers or probes) are operably joined to an endogenous or exogenous regulatory region to form an expression construct. Useful regulatory regions for these purposes include the endogenous Hv1 regulatory region, constitutive promoter sequences (e.g., CMV, SV40, EF2), and inducible promoter sequences (e.g., lacZ, tet). Many useful vector systems are commercially available. For example, useful bacterial vectors include, but are not limited to, pQE70, pQE60, pQE-9 (Qiagen, Valencia, Calif.), pBluescript II™ (Stratagene, La Jolla, Calif.), and pTRC99a, pKK223-3, pDR540 and pRIT2T (Pharmacia, Piscataway, N.J.), pTrc (Amann et al. (1988), *Gene* 69:301-315) and pET 11d (Studier et al. (1990), *Methods in Enzymol.* 185:60-89). Examples of vectors for expression in yeast include pYepSec1 (Baldari et al. (1987), *EMBO J.* 6:229-234), pMFa (Kuijan et al. (1982), *Cell* 30:933-943), pJRY88 (Schultz et al. (1987), *Gene* 54:113-123), and pYES2 (Invitrogen Corporation, San Diego, Calif.). The Hv1 proteins can also be expressed in insect cells (e.g., Sf 9 cells) using, for example, baculovirus expression vectors including, but not limited to, pAc vectors (Smith et al. (1983), *Mol. Cell. Biol.* 3:2156-2165) and pVL vectors (Lucklow et al. (1989), *Virology* 170: 31-39). Examples of mammalian expression vectors include, but are not limited to, pCDM8 (Seed (1987), *Nature* 329:840) and pMT2PC (Kaufman et al. (1987), *EMBO J.* 6:187-195). Other useful eukaryotic vectors include, but are not limited to, pXT1, pSG5 (Stratagene, La Jolla, Calif.), and pSVK3, pBPV, pMSG, and PSVLSV40 (Pharmacia, Piscataway, N.J.). Other vectors are described in the examples below. Thus, one of ordinary skill in the art can choose a vector system appropriate to the host cell to be transformed.

In some embodiments, the vectors comprise defective or partial Hv1 sequences in a "knock-out" vector. Such vectors are well-known in the art and can be used to produce a transgenic organism in which an endogenous gene is "knocked-out" by recombination with a partially homologous exogenous sequence which introduces a mutation within the endogenous sequence. Typically, the vector is directed at an endogenous target sequence which can be all or part of a gene of interest. The vector includes 5' and 3' flanking sequences which are homologous to the 5' and 3' ends of the target. Between the 5' and 3' flanking sequences is the sequence including the mutation. The mutation can be a termination mutation, frame-shift mutation, large deletion, or even the introduction of a new coding sequence which serves both to disrupt the endogenous gene and to act as a marker to identify successful homologous recombinants. Knock-out vectors are further discussed below.

In another series of embodiments, the Hv1 coding sequences can be joined to regulatory regions and exogenous coding sequences to form a genetic construct or fusion vector which encodes a fusion protein. In some embodiments, the Hv1 coding sequences can be joined to exogenous coding sequences that confer new and useful properties to the fusion protein. For example, fusion vectors and fusion proteins can be useful to increase the expression of the Hv1 protein, to increase the solubility of the Hv1 protein, or to aid in the purification of the Hv1 protein (e.g., by providing a ligand sequence for affinity purification). A proteolytic cleavage site can be introduced at the junction of the Hv1 and the non-Hv1 protein sequences so that the Hv1 protein can easily be separated from the fusion moiety. Typical fusion expression vectors include pGEX (Smith et al. (1988), *Gene* 67:31-40), pMAL (New England Blolabs, Beverly, Mass.) and pRIT5 (Pharmacia, Piscataway, N.J.) which fuse glutathione S-transferase (GST), maltose E binding protein, or protein A, respectively, to the target recombinant protein.

In another series of embodiments, genetic constructs are produced in which the coding region from a reporter gene is operably joined to the regulatory region of a Hv1 gene. Such genetic constructs are useful in assays to identify or characterize compounds that enhance or repress Hv1 gene expression by enhancing or repressing transcription of the Hv1 gene. A wide variety of suitable reporter genes are known to those of skill in the art, and are commercially available. Examples include, but are not limited to, the lacZ, luciferase and green fluorescent protein (GFP) genes.

Useful Hv1 regulatory elements include sequences having at least 80% nucleotide identity to at least 100-1,000,200-800 or 300-700 consecutive nucleotides selected from the 1,000 nucleotides immediately 5' to the Hv1 transcription initiation site. Useful regulatory elements retain the ability to promote transcription of a coding sequence operably joined to the element in a mammalian cell in which a Hv1 gene is expressed. In particular, useful regulatory elements retain the ability to promote transcription in cells in which the Hv1 gene from which the element was derived is expressed, or in which a homolog of that Hv1 gene is expressed.

Transformed Cell Lines

In another aspect, the present invention provides cell lines transformed with the nucleic acid molecules of the invention. Such cell lines can simply propagate these nucleic acids (e.g., when transformed with cloning vectors) or can express the polypeptides encoded by these nucleic acids (e.g., when transformed with expression vectors). Such transformed cell lines can be used to produce the Hv1 proteins and the Hv1 protein fragments of the invention, or can be used in assays to screen for compounds that increase (i.e., enhance) or decrease (i.e., repress) Hv1 protein expression, or which increase (i.e., agonize) or decrease (i.e., antagonize) Hv1 protein activity.

The transformed cells can be produced by introducing into a cell an exogenous nucleic acid or nucleic acid analog which replicates within that cell, that encodes a polypeptide sequence which is expressed in that cell, and/or that is integrated into the genome of that cell so as to affect the expression of a genetic locus. The transformation can be achieved by any of the standard methods referred to in the art as transformation, transfection, transduction, electroporation, ballistic injection, and the like. The method of transformation is chosen to be suitable to the type of cells being transformed and the nature of the genetic construct being introduced into the cells.

Useful cell lines for transformation include bacterial cells (e.g., *Escherichia coli*), yeast cells (e.g., *Saccharomyces cerevisiae*), insect cells (e.g., *Drosophila melanogaster* Schneider cells), nematode cells (e.g., *Caenorhabditis elegans*), amphibian cells (e.g., *Xenopus* oocytes), rodent cells (e.g., murine 3T3 fibroblasts, CHO cells), and human cells (e.g., skin fibroblasts, embryonic kidney cells). Cells with a substantial native current are less desirable for transformation (e.g., HL 60 cells, or pulmonary or blood-derived cell lines) and, conversely, cells with little or no native current are preferred (e.g., HEK-293, NM1 or COS cells). Yeast two hybrid approaches and co-immunoprecipitation approaches can be used to screen libraries to identify Hv1 accessory, associating or interacting proteins, including modulators of Hv1 activity.

Appropriate cells can be transformed with any of the above-described genetic constructs in order to produce Hv1 proteins, including fragments of Hv1 proteins, fusion proteins of Hv1 proteins, or reporter genes under the control of a Hv1 regulatory region.

The cells can be transformed according to any method known in the art appropriate to the cell type being transformed. Appropriate methods include those described generally in, e.g., Sambrook et al. (1989), *Molecular Cloning: A Laboratory Manual*, Cold Spring Harbor Laboratories, New York; and Davis et al. (1986), *Basic Methods in Molecular Biology*, Elsevier. Particular methods include calcium phosphate co-precipitation (Graham et al. (1973), *Virol.* 52:456-467), direct micro-injection into cultured cells (Capecchi (1980), *Cell* 22:479-488), electroporation (Shigekawa et al. (1988), *BioTechniques* 6:742-751), liposome-mediated gene transfer (Mannino et al. (1988), *BioTechniques* 6:682-690), lipid-mediated transduction (Feigner et al. (1987), *Proc. Natl. Acad. Sci. USA* 84:7413-7417), and nucleic acid delivery using high-velocity microprojectiles (Klein et al. (1987), Nature 327:70-73).

In another aspect, cells transformed to express Hv1 can be used as research tools in the study of non-electrogenic transporters. The Hv1 channel responds to both transmembrane voltage and pH gradients, and extrudes protons from the cytoplasm into the extracellular space when activated. Because Hv1 is an ion channel, it provides a measurable electrical signal. Thus, Hv1-dependent electrical signals can be used to assay non-electrogenic changes in pH, such as those due to the Na+/H+ exchanger or H+/Cl--anti-porter protein. Specifically, by changing extracellular and/or intracellular conditions (e.g., concentration of a test compound), the activity of a large number of other non-electrogenic transporters that effect intracellular pH changes can be assayed as current in Hv1-transformed cells. Indeed, the activity of any biomolecule that creates free intracellular H+ could be assayed by using Hv1 to convert changes in proton concentrations or pH into electrical currents which are more easily assayed. The non-electrogenic biomolecule can cause an decrease in intracellular pH which activates the Hv1 protein and increases a detectable electrical signal, or can cause an increase in intracellular pH which deactivates the Hv1 protein and decreases a detectable electrical signal.

Transgenic Animals

The present invention also provides for the production of transgenic non-human animal models in which wild type, mutant, fusion, chimeric, or antisense Hv1 sequences are expressed, or in which Hv1 sequences have been inactivated or deleted (e.g., "knock-out" constructs) or replaced with reporter or marker genes (e.g., "knock-in reporter" constructs). The Hv1 sequences can be conspecific to the transgenic animal (e.g., murine sequences in a transgenic mouse) or transpacific to the transgenic animal (e.g. human sequence in a transgenic mouse). In such a transgenic animal, the transgenic sequences can be expressed inducibly, constitutively or ectopically. Expression can be tissue-specific or organism-wide. Engineered expression of Hv1 sequences in tissues and cells not normally containing Hv1 gene products can cause novel alterations of proton flux and lead to novel cell or tissue phenotypes. Ectopic or altered levels of expression of Hv1 sequences can alter cell, tissue and/or developmental phenotypes. Transgenic animals are useful as models of disorders arising from defects in Hv1 activity.

Transgenic animals are also useful for screening compounds for their effects on Hv1 activity. Transgenic animals transformed with reporter constructs can be used to measure the transcriptional effects of small molecules or drugs or physical perturbations on the expression of Hv1 genes and proteins in vivo. The transgenic animals of the invention, can be used to screen such compounds for therapeutic utility.

Animal species suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) can be used due to their relative ease of maintenance and shorter life spans. Transgenic non-human primates can be used for longer term studies due to their greater similarity to humans.

Using the nucleic acids disclosed and otherwise enabled herein, there are several embodiments of the creation of a transgenic animal. Thus, useful animal models include at least the following: (1) animals in which sequences encoding at least a functional fragment of a Hv1 gene has been recombinantly introduced into the genome of the animal as an additional gene, under the regulation of either an exogenous or an endogenous promoter element, and as either a minigene (i.e., a genetic construct of the Hv1 gene based on cDNA with introns removed) or a large genomic fragment; (2) animals in which sequences encoding at least a functional fragment of a Hv1 gene have been recombinantly substituted for one or both copies of the animal's endogenous Hv1 gene by homologous recombination or gene targeting; (3) animals in which one or both copies of one of the animal's homologous Hv1 genes have been recombinantly "humanized" by the partial substitution of sequences encoding the human homolog by homologous recombination or gene targeting; (4) animals in which sequences encoding a reporter gene have replaced the endogenous Hv1 gene by homologous recombination; (5) and "knock-out" animals in which one or both copies of the animal's Hv1 sequences have been partially or completely inactivated by the insertion, deletion or substitution of one or more nucleotides by homologous recombination. These and other transgenic animals of the invention are useful as models of conditions or disorders arising from defects in the Hv1 gene and/or protein, insufficient or excessive expression of the Hv1 channel, or insufficient or excessive activity of the Hv1 channel. These animals are also useful for screening compounds for their effects on the Hv1 gene and/or protein.

To produce an animal model (e.g., a transgenic mouse), a wild type or allelic variant Hv1 sequence or a wild type or allelic variant of a recombinant nucleic acid encoding at least a functional fragment of a Hv1 protein can be inserted into a germ line or stem cell using standard techniques of oocyte or embryonic stem cell microinjection, or other methods of transformation of such cells. Alternatively, other cells from an adult organism can be employed. Animals produced by these or similar processes are referred to as transgenic. Similarly, if it is desired to inactivate or replace an endogenous Hv1 sequence, homologous recombination using oocytes, embryonic stem or other cells can be employed. Animals produced by these or similar processes are referred to as "knock-out" (inactivation) or "knock-in" (replacement) models.

For oocyte injection, one or more copies of the recombinant DNA constructs of the present invention can be inserted into the pronucleus of a just-fertilized oocyte. This oocyte is then reimplanted into a pseudo-pregnant foster mother. Alternatively, embryonic stem cells can be transformed, and the transformed stem cells are injected into a wild-type blastocyst, which is then reimplanted into a pseudo-pregnant foster mother. The live born animals are screened for integrants using standard DNA/mRNA analysis (e.g., from the tail veins of offspring mice) for the presence of the inserted recombinant transgene sequences. The transgene can be either a complete genomic sequence introduced into a host as part of a yeast artificial chromosome (YAC), bacterial artificial chromosome (BAC), or other chromosome DNA fragment; as a cDNA with either the endogenous promoter or a heterologous promoter; or as a minigene containing all of the coding regions and other elements found to be necessary for optimum expression.

To create a transgene, the target sequence of interest (e.g., a wild type or allelic variant of a Hv1 sequence) is typically ligated into a cloning site located downstream of a promoter element which will regulate the expression of RNA from the sequence. Downstream of the coding sequence, there is typically a polyadenylation sequence. An alternative approach to creating a transgene is to use an exogenous promoter and regulatory sequences to drive expression of the transgene. Finally, it is possible to create transgenes using large genomic DNA fragments such as YACs which contain the entire desired gene as well as its appropriate regulatory sequences.

Animal models can be created by targeting endogenous Hv1 sequences for homologous recombination. These targeting events can have the effect of removing an endogenous sequence (knock-out) or altering the endogenous sequence to create an amino acid change associated with human disease or an otherwise abnormal sequence (e.g., a sequence which is more like the human sequence than the original animal sequence) (knock-in animal models). A large number of vectors are available to accomplish such changes, and appropriate sources of genomic DNA for mouse and other animals are commercially available (e.g., GenomeSystems Inc., St. Louis, Mo.).

The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out.

Early embryos can also be transfected to insert the recombinant DNA constructs of the invention. In this method, the transgene (e.g., a wild type or allelic variant of a Hv1 sequence) is inserted into a viral or retroviral vector which is used to directly infect embryos (e.g., mouse or non-human primate embryos) during the early stages of development to generate partially transgenic animals. Some of the partially transgenic animals will bear the transgenes in germ line cells and can be bred to produce fully transgenic animals.

Alternatively, homologous recombination using a population of stem cells allows for the screening of the population for successful transformants. Once identified, these can be injected into blastocysts, and a proportion of the resulting animals will show germ line transmission of the transgene. These partially transgenic animals can be bred to produce fully transgenic animals.

Techniques of generating transgenic animals, as well as techniques for homologous recombination or gene targeting, are now widely accepted and practiced. A laboratory manual on the manipulation of the mouse embryo, for example, is available which details standard laboratory techniques for the production of transgenic mice (Hogan et al. (1986), *Manipulating the Mouse Embryo*, Cold Spring Harbor Laboratory Press, Cold Spring Harbor, N.Y.).

Hv1 Proteins and Polypeptides

In another aspect, the present invention provides substantially pure preparations of Hv1 proteins. The proteins can be isolated from immune tissues such as lymph nodes, B-lymphocytes, monocytes and spleen, using standard techniques such as immunoaffinity purification with the antibodies of the invention (see below), or can be isolated from the transformed cells of the invention, in which they can be expressed at higher levels and, optionally, as fusion proteins which are more easily isolated and/or purified.

In some embodiments, the Hv1 proteins comprise the entire translated sequence of the Hv1 coding region. Examples of such full-length Hv1 proteins include the human Hv1 protein disclosed as SEQ ID NO: 2 and the various homologs disclosed as SEQ ID NOs: 4, 6, 8, 10, 12, 14, 16, 18, 20 and 22, as well as allelic and non-human homologs of Hv1 proteins, and functional equivalents thereof.

In other embodiments, the Hv1 proteins are Hv1 fragments. Such fragments include the structural domains of the Hv1 proteins, including the transmembrane and loop-forming regions of the proteins, as well as N-terminally and/or C-terminally truncated variants of the protein. Useful structural domains include the transmembrane domains of the human Hv1 protein (e.g., approximately residues 101-125, 137-161, 172-190, and 200-220 of SEQ ID NO: 2; and allelic variants and homologs thereof), the extracellular loops between transmembrane domains (e.g., approximately residues 126-136, 162-171, and 191-199 of SEQ ID NO: 2; and allelic variants and homologs thereof). Particularly useful fragments include all of the transmembrane domains and loops between the transmembrane domains, but lack all or part of the N-terminal and/or C-terminal intracellular domains. Other Hv1 fragments include potentially useful epitopes of the Hv1 proteins, as identified by standard sequence analysis techniques. Thus, for example, useful Hv1 fragments include the following human Hv1 sequences: residues 1-29, 32-68, 78-100, 126-136, 191-199, 221-237 and residues 241-273 of SEQ ID NO: 2. Other useful fragments include allelic variants of these epitopes, as well as the corresponding residues of the non-human homologs shown in the sequence alignment of FIG. 2.

In certain embodiments, polypeptides are provided having at least 80%, 85%, 90% or 95% amino acid sequence identity with at least a structural domain of an Hv1 protein. Thus, in some embodiments, a polypeptide is provided having at least 80%, 85%, 90% or 95% amino acid sequence identity with one or more transmembrane domains of an Hv1 protein (e.g., approximately residues 101-125, 137-161, 172-190, and 200-220 of SEQ ID NO: 2; and allelic variants and homologs thereof), and/or one or more loop between transmembrane domains (e.g., approximately residues 126-136, 162-171, and 191-199 of SEQ ID NO: 2; and allelic variants and homologs thereof). In some embodiments, polypeptides are provided having at least 80%, 85%, 90% or 95% amino acid sequence identity with a Hv1 protein and having Hv1 activity. The ability of a protein to exhibit Hv1 activity can be measured by its ability to complement an Hv1−/−mutant (e.g., a Hv1 knock-out mutant) and restore a normal or Hv1+/+phenotype (e.g., to restore proton flux) in a cell otherwise capable of expressing Hv1 activity (e.g., an immune tissue cell from the Hv1−/−mutant).

In certain embodiments, the polypeptides of the invention include an Hv1 sequence of at least 50 amino acid residues in length, or at least 100, 150, 200, 250 or 300 amino acid residues in length, or any other length in the range of 50-300. These polypeptides can include an Hv1 sequence which includes at least one transmembrane domain, at least one loop domain, or combinations thereof. In some embodiments, the polypeptide has Hv1 activity. Such activity can include the induction of proton currents; mediation of hydrogen peroxide generation; and/or restoration of proton flux when expressed in a cell (e.g., an oocyte, HEK cell, or CHO cell).

Antibodies Against Hv1 Proteins and Polypeptides

In another aspect, the present invention provides substantially pure preparations of antibodies against Hv1 proteins, or epitopes thereof, and methods of making such antibodies. The antibodies can be polyclonal or monoclonal, and can be made by methods well known in the art. In particular, the invention provides antibodies raised against Hv1 epitopes having high predicted antigenicity, which therefore will selectively bind to and, thereby, isolate or identify wild type and/or variant forms of the Hv1 proteins.

The antibodies can be raised against the full-length Hv1 proteins, against fragments of the Hv1 proteins, or using any Hv1 epitopes which are characteristic of the proteins and which substantially distinguish them from other proteins. In certain embodiments, the antibodies are raised against Hv1 epitopes including, but not limited to, residues 1-29, 32-68, 78-100, 126-136, 191-199, 221-237 and residues 241-273 of SEQ ID NO: 2. Other useful epitopes include allelic variants and non-human homologs of these epitopes (e.g., corresponding epitopes identified in the alignment of homologs of FIG. 2). Epitopes having a high predicted antigenicity can be identified by prediction of hydrophobicity, surface probability and antigenic index using standard programs, including GCG and MacVector (Genetics Computer Group, University of Wisconsin Biotechnology Center, Madison, Wis.; Accelrys Inc., San Diego, Calif.). See also, Jameson and Wolf (1988), *Comput. Appl. Biosci.* 4:181-186.

Hv1 immunogen preparations can be produced from crude extracts (e.g., membrane fractions of cells expressing the proteins), from proteins or peptides substantially purified from cells which naturally or recombinantly express them or, for small immunogens, by chemical peptide synthesis. The Hv1 immunogens also can be in the form of a fusion protein in which the non-Hv1 portion is chosen for its adjuvant properties (e.g., KLH) and/or its ability to facilitate purification (e.g., polyhistidine sequences).

The antibodies of the invention can be polyclonal or monoclonal, or can be antibody fragments, including Fab fragments, F(ab')$_2$ fragments, Fv fragments, and single chain Fv fragments (scFv). In addition, after identifying useful antibodies by the method of the invention, recombinant antibodies can be generated, including any of the antibody fragments listed above, as well as chimeric and/or humanized antibodies based upon non-human antibodies to the Hv1 proteins: In light of the present disclosure of Hv1 proteins, as well as the characterization of homologous proteins enabled herein, one of ordinary skill in the art can produce the above-described antibodies by any of a variety of standard means. For an overview of antibody techniques, see *Antibody Engineering*, 2nd Ed., Borrebaek, ed., Oxford University Press, Oxford (1995).

As a general matter, monoclonal anti-Hv1 antibodies can be produced by first injecting a mouse, rabbit, goat or other suitable animal with an Hv1 immunogen in a suitable carrier or diluent. Carrier proteins or adjuvants can be utilized, and booster injections (e.g., bi- or tri-weekly over 8-10 weeks) can be employed as necessary. After allowing for development of a humoral response, the animals are sacrificed and their spleens are removed and resuspended in an appropriate buffer (e.g., phosphate buffered saline). The spleen cells serve as a source of lymphocytes, some of which will produce antibodies of the appropriate specificity. These cells are then fused with an immortalized cell line (e.g., a myeloma), and the products of the fusion are plated into tissue culture wells in the presence of a selective agent (e.g., HAT). The wells are serially screened and replated, selecting cells making a useful antibody each time. Typically, several screening and replating procedures are carried out until the wells contain single clones which are positive for antibody production. Monoclonal antibodies produced by such clones can be purified by standard methods such as affinity chromatography using Protein A Sepharose, by ion-exchange chromatography, or by variations and combinations of these techniques.

The antibodies of the invention can be used in a variety of applications. For example, antibodies can be used in a purification process (e.g., immunoaffinity purification) for Hv1 proteins, in assays to detect the presence or level of Hv1 proteins (e.g., in a diagnostic test for a Hv1-related disorder), or in assays to measure the presence or level of Hv1 expression in transformed cells (e.g., in assays for regulators of Hv1 expression, in Western blotting to identify cells expressing Hv1 proteins, or in immunocytochemistry or immunofluorescence techniques to establish the cellular or extracellular location of Hv1 proteins).

The antibodies of the invention can be bound to or conjugated with other compounds or materials for diagnostic and/or therapeutic uses. For example, they can be coupled to labels such as radionuclides, fluorescent compounds (e.g., rhodamine), or enzymes for imaging or therapy. The labels can be bound to the antibodies covalently or non-covalently.

In another aspect, the invention provides kits for detecting at least an epitope of a Hv1 protein. The kits include an anti-Hv1 antibody and a means for detecting the antibody. The means for detecting the antibody can be a detectable label bound to the antibody or secondary antibodies for detecting the anti-Hv1 antibodies (e.g., a labeled goat anti-rabbit-Ig antibody as a secondary antibody for detecting a rabbit anti-Hv1 antibody).

Assays for Modulators of Hv1 Expression or Activity.

In another aspect, the present invention provides assays for modulators of Hv1 expression or activity. The modulators can affect the transcription, translation, post-translational processing, localization, or activity of a Hv1 gene and/or protein.

Thus, in one series of embodiments, cells naturally-expressing the Hv1 protein or the transformed cells of the invention are contacted with a candidate compound, and the effect of the compound on the expression or activity of Hv1 is determined. As a general matter, the assays require contacting a candidate compound with a cell expressing an Hv1 protein and measuring an indicator of Hv1 activity in the cell. The indicator can be an indicator of transcription (e.g., mRNA levels), translation (e.g., protein levels), post-translational processing (e.g., specific glycosylation), localization (e.g., immunohistochemistry), or activity (e.g., current, proton flux, intracellular pH). The indicator measurement is then compared to a reference level to determine whether the candidate compound caused an increase or decrease in the indicator. The reference level can be extrinsic (e.g., a predetermined baseline level) or intrinsic (e.g., a measurement of the same cell prior to contact with the candidate compound, or measurement of an untreated control cell) to the assay. If an increase or decrease is significant (based on a single reading or on multiple readings from one or more cells), the candidate compound is identified as a potential modulator of Hv1 activity. Assays for changes in Hv1 expression or activity can include any of those used routinely in the art for other genes, or other proteins having ion channel activity. For example, changes in the presence or levels of Hv1 mRNA or protein can be detected to identify enhancers or repressors of Hv1 expression. Alternatively, when using a reporter gene construct of the invention, the biochemical or phenotypic change characteristic of the reporter can be used as an indication that the candidate compound enhances or represses reporter gene expression. In other embodiments, changes in the activity of the Hv1 protein can be detected by measuring, for example, the flux of protons mediated by the Hv1 protein, production of hydrogen peroxide mediated by the Hv1 protein, depletion of superoxide anions mediated by Hv1 protein, whole cell or channel currents, and/or intracellular pH. Measurements of proton fluxes can be facilitated by the use of chromophores which change color depending upon the concentration of specific ions or pH.

If the transformed cells of the invention are first used to identify candidate compounds, the effects of the candidate compounds on cells naturally-expressing the Hv1 channel can be tested to confirm or validate results obtained in the transformed cells.

Compounds which bind to Hv1 are candidates for modulating Hv1 activity. Thus, in another series of embodiments, libraries of compounds can be screened to identify candidates for modulating Hv1 activity by contacting candidate compounds with an Hv1 protein, or at least a structural domain of an Hv1 protein, to identify compounds that bind to Hv1. Hv1 structural domains which can be used in these methods include transmembrane domains, and particularly extracellular loop regions. In such methods, the Hv1 protein or Hv1 structural domain can be immobilized (e.g., on a column or microparticle) and a solution of the candidate compound can be contacted with the Hv1 moiety, or the candidate compound can be immobilized (e.g., on a column or microparticle) and a solution of the Hv1 moiety can be contacted with the candidate compound. Alternatively, in some embodiments, neither the candidate compound nor the Hv1 moiety is immobilized but, rather, both are in solution and binding is detected by, for example, aggregation of particles bearing the binding partners. Binding can be detected by a variety of methods well known in the art (e.g., radioactive or fluorescent labeling of one component of the potential binding pair; plasmon-resonance detection of binding; turbidity changes in aggregation assays). Compounds which, under physiological conditions (e.g., within the immune tissues, hippocampal neurons), exhibit significant binding (e.g., $K_d \leq 10$ μM) to an Hv1 protein, are potential modulators of Hv1 activity.

In certain embodiments, the assay to identify agents which agonize Hv1 activity is conducted using wild type Hv1. In other embodiments, the assay to identify agents which agonize Hv1 activity is conducted using a mutant Hv1. Mutant Hv1 proteins useful in this aspect include those which have been modified in order to produce a more easily detected indicator of activity, such as a change in coor or absorption of a chromophore.

Candidate agonists and antagonists, or combinations thereof, can be tested for efficacy and toxicity in animal models. Preclinical testing can also establish a mechanism of action for the drug, its bioavailability, absorption, distribution, metabolism, and elimination through studies performed in vitro (that is, in test tubes, beakers, petri dishes, etc.) or in vivo in animals. Animal studies are used to assess whether the drug will provide the desired results. Varying doses of the experimental drug are administered to test the drug's efficacy, identify harmful side-effects that may occur, and evaluate toxicity.

Methods of Hv1 Genotyping and Diagnosing Hv1-Related Disorders

In another aspect, the present invention provides methods for genotyping subjects with respect to the Hv1 gene, and diagnosing Hv1-related disorders such as infertility. Thus, for example, the Hv1 nucleic acids (or a portion thereof) of a subject can be tested to ascertain whether that subject's Hv1 genotype includes any mutations in the sequences relative to wild-type. Of particular significance would be mutations which introduce termination or frame-shift mutations that prevent the production of functional Hv1 proteins. However, point mutations that cause decreased Hv1 activity can also be identified. Similarly, the antibodies of the present invention can be used to test the immune tissue of a subject to determine the presence or level of Hv1 proteins. Of particular note would be an absence or significant decrease in the level of Hv1 protein. In some instances, point mutations can be detected by antibodies which are specific for epitopes including or affected by the mutant sequences. Determination of a subject's Hv1 genotype can be used for genetic counseling, or for diagnosing a disease or disorder that results from an Hv1 defect.

To determine a subject's Hv1 genotype, or for diagnosing an Hv1-related disorder, the nucleic acids of the invention can be used as primers in polymerase chain reaction (PCR) (e.g., anchor PCR or RACE PCR), or ligase chain reaction (LCR) amplifications of the subject's DNA/mRNA. See, e.g., U.S. Pat. No. 4,683,195 and U.S. Pat. No. 4,683,202; Landegran et al. (1988), *Science* 241:1077-1080; Nakazawa et al. (1994), *Proc. Natl. Acad. Sci. USA* 91:360-364; and Abravaya et al. (1995), *Nucleic Acids Res.* 23:675-682. Other useful methods for amplifying a subject's DNA/mRNA using the nucleic acids of the invention include self-sustained sequence replication (e.g., Guatelli et al. (1990), *Proc. Natl. Acad. Sci. USA* 87:1874-1878), transcriptional amplification (e.g., Kwoh et al. (1989), *Proc. Natl. Acad. Sci. USA* 86:1173-1177), and Q-Beta Replicase-based systems (e.g., Lizardi et al. (1988), *Bio/Technology* 6:1197. The presence, absence or size of the resulting amplification products (e.g., Saiki et al. (1986), Nature 324:163; Saiki et al. (1989), *Proc. Natl. Acad. Sci. USA* 86:6230; Gibbs et al. (1989), *Nucleic Acids Res.* 17:2437-2448; Prossner (1993), *Tibtech* 11:238; Gasparini et al. (1992), *Mol. Cell. Probes* 6:1; Barany (1991) *Proc. Natl. Acad. Sci. USA* 88:189), direct sequencing of the amplification products (e.g., Maxim and Gilbert (1977), *Proc. Natl. Acad. Sci. USA* 74:560; Sanger (1977), *Proc. Natl. Acad. Sci. USA* 74:5463), and other standard analytic techniques can be employed to determine Hv1 genotypes. The amplified products also can be used in many of the techniques described below.

The nucleic acids of the invention also can be used as probes in hybridization and/or conformation-based assays to identify complementary or imperfectly complementary sequences in a subject.

For example, in some embodiments, mutations can be identified by selectively hybridizing sample nucleic acids to immobilized control nucleic acids. The controls can be adsorbed to filters or columns, or can be arranged in ordered arrays containing one or more, or even thousands, of oligonucleotides probes (see, e.g., Cronin et al. (1996), *Human Mutation* 7:244-255; Kozal et al. (1996), *Nature Medicine* 2:753-759).

In other embodiments, enzymatic or chemical cleavage can be employed to cleave or restrict duplexes of sample and control sequences at mismatched bases (e.g., Myers et al. (1985), *Science* 230:1242). For example, RNA/DNA duplexes can be treated with RNAse; DNA/DNA hybrids can be treated with S1 nuclease to digest duplexes at mismatched bases; G/A mismatches are cleaved at the A by the *E. coli* mutY enzyme; and G/T mismatches are cleaved at the T by the human thymidine DNA glycosylase (see, e.g., Hsu et al. (1994), *Carcinogenesis* 15:1657-1662). Chemical cleavage of mismatches can be employed using, for example, hydroxylamine, osmium tetroxide and/or piperidine. See generally, e.g., Cotton et al. (1988), *Proc. Natl. Acad. Sci. USA* 85:4397; Saleeba et al. (1992), *Methods Enzymol.* 217:286-295; and U.S. Pat. No. 5,459,039.

In other embodiments, mutations can create or destroy specific sequences which serve as cleavage points for restriction enzymes, ribozymes or deoxyribozymes. Thus, restriction fragment length polymorphism (RFLP) analysis can be employed in which (amplified) sample DNA is digested with at least one restriction endonuclease, and the resulting fragment lengths are analyzed and compared to controls to determine the presence or absence of mutations which affect the pattern of restriction fragment lengths. Similarly, sequence-specific ribozymes (or deoxyribozymes) can be used to identify mutations that create or destroy ribozyme (or deoxyribozymes) cleavage sites. See, e.g., U.S. Pat. No. 5,498,531.

In other embodiments, mutations can be detected by their effects on the electrophoretic mobility of a sequence, either as a single-stranded nucleic acid or as a duplex. For example, single-strand conformation polymorphism (SSCP) analysis (Orita et al. (1989), *Proc. Natl. Acad. Sci. USA* 86:2766; Cotton (1993), *Mutat. Res.* 285:125-144; Hayashi (1992), *Genet. Anal. Tech. Appl.* 9:73-79; and Keen et al. (1991), *Trends Genet.* 7:5), denaturing gradient gel electrophoresis (DGGE) (Myers et al. (1985), *Nature* 313:495), and temperature gradient gel electrophoresis (Rosenbaum and Reissner (1987), *Biophys. Chem.* 265:12753) can be employed.

These and other methods of detecting mutations in the Hv1 genes and proteins will be apparent to one of ordinary skill in the art based upon the nucleic acid and protein sequences disclosed herein.

Physiological Processes and Conditions Relating to Hv1 Activity

The tissue distribution and voltage-gated proton channel activity of Hv1 suggest that the Hv1 channel could be implicated in the etiology and/or treatment of a number of conditions involving proton flux, acid secretion, and/or pH maintenance.

Cellular Immune Response

Hv1 appears to play a role in sustaining superoxide anion production in activated phagocytes and, therefore, appears to be important in innate immune function. The function of voltage-gated proton channels in phagocytes is intertwined intimately with that of NADPH oxidase. In unstimulated cells, this enzyme complex is not only inactive, but also physically unassembled, with components segregated in the membrane and in the cytosol. Upon challenge with a variety of agents, it assembles and becomes active, converting oxygen, $O_2$, to superoxide anion, $O_2^-$, which exerts limited bactericidal activity itself but, more importantly, is a precursor to even more reactive species such as $H_2O_2$ and HOCl. This process is called the "respiratory burst" because one manifestation is increased oxygen consumption by phagocytes.

Human T and B lymphocytes, as well as the intensely studied Jurkat cell line, all express voltage-gated proton channels. H+ currents in T lymphocytes are small, ~1.5 pA/cell, but are 100 times larger in both Jurkat cells and B lymphocytes. H+ channel expression correlates with the capacity to produce superoxide anion. Presumably, H+ channels perform the same function in lymphocytes that they do in phagocytes of charge compensation during NADPH oxidase activity. One day after stimulation with immune activator PMA (phorbol 12-myristate 13-acetate), H+ currents in T lymphocytes increased 13-fold, perhaps a reflection of the cell gearing up for greater metabolic activity. Thus, an Hv1 agonist would be expected to stimulate immune response and be useful for an immunocompromised subject.

The importance of a functional NADPH oxidase in promoting phagocytic killing of bacteria, parasites, and other invaders is demonstrated by the clinical morbidity and mortality associated with its deficiency in chronic granulomatous disease (CGD). Thus, an Hv1 agonist would be expected to aid the respiratory burst and be useful in treating or preventing chronic granulomatous disease.

Microglial cells are the main resident immune cells in the central nervous system, and normally perform a scavenging role analogous to macrophages. In their resting state, microglial cells are highly ramified, but upon activation they become amoeboid, more macrophage-like, and capable of phagocytosis. In Alzheimer's disease, activated microglial cells are associated with dying neurons and amyloid plaques, and microglial activation has been implicated in sustaining a local inflammatory response in other neurodegenerative diseases. Therefore, increased or defective Hv1 function could be related to neurodegenerative diseases, and decreased or corrected Hv1 function could be therapeutic.

Inflammatory Response

Inflammation is a normal response of the body to protect tissues from infection, injury or disease. The inflammatory response begins with the production and release of chemical agents by cells in the infected, injured or diseased tissue. These agents cause redness, swelling, pain, heat and loss of function. Inflamed tissues generate additional signals that recruit leukocytes to the site of inflammation. Leukocytes destroy any infective or injurious agent, and remove cellular debris from damaged tissue. This inflammatory response usually promotes healing but, if uncontrolled, may become harmful.

The inflammatory response can be either acute or chronic. Acute inflammation typically lasts only a few days. The treatment of acute inflammation, where therapy includes the administration of aspirin and other non-steroidal anti-inflammatory agents, provides relief of pain and fever for patients. In contrast, chronic inflammation lasts weeks, months or even indefinitely and causes tissue damage. In chronic inflammation, the inflammation becomes the problem rather than the solution to infection, injury or disease. Chronically inflamed tissues continue to generate signals that attract leukocytes from the bloodstream. When leukocytes migrate from the bloodstream into the tissue they amplify the inflammatory response. This chronic inflammatory response can break down healthy tissue in a misdirected attempt at repair and healing. Conditions characterized by chronic inflammation include, among others: atherosclerosis, including coronary artery disease; rheumatoid arthritis and osteoarthritis; asthma; and solid organ transplant rejection.

Thus, an Hv1 agonist may be expected to accelerate the destruction of infective or injurious agents, or the removal of cellular debris, and be useful for reducing the inflammatory response in a subject.

At the same time, inflammatory responses can also be affected by acid secretion by the inflammatory response cells in the blood. Therefore, depending upon the need to increase or decrease the inflammatory response, an Hv1 agonist or antagonist might be expected to be useful for the treatment of such conditions.

CO2 Exchange

The high density of Hv1 channels in alveolar and airway epithelium in the lungs suggests that Hv1 may play a role in facilitating $CO_2$ exchange, and the elimination of $CO_2$ from the body.

Although it is usually assumed that $CO_2$ simply diffuses across the apical membranes, certain epithelial cells have low $CO_2$ permeability. In addition, the rate of spontaneous recombination of $H^+$ and $HCO_3^-$ in the alveolar subphase (liquid lining the alveolus) is likely to be too slow to account for more than a tiny fraction of the total $CO_2$ elimination, because this fluid lacks the enzyme carbonic anhydrase (see DeCoursey, supra). The exit of $H^+$ and $HCO_3^-$ provides an alternative pathway. Thus, $CO_2$ movement is accomplished by utilizing separate pathways for the flux of bicarbonate anion ($HCO_3$) and protons ($H^+$), with which $CO_2$ is in equilibrium in aqueous solutions. On each passage through the systemic circulation, $CO_2$ is taken up, converted to $HCO_3^-$ and brought to the lungs, where $CO_2$ is reconstituted and eliminated. Extrusion of $H^+$ through proton channels is believed to be accompanied by $HCO_3^-$ extrusion. By increasing the flux of protons across the alveolar membranes, Hv1 may act to increase the flux of bicarbonate anions. Therefore, decreased or defective Hv1 function could be related to decreased $CO_2$ exchange, leading to decreased respiratory function and resultant plasma acidosis, and increased or corrected Hv1 function could be therapeutic for conditions such as chronic obstructive pulmonary disease (COPD).

Conversely, a voltage-gated proton conductance has been reported in the cystic fibrosis JME/CF15 airway cell line, along with evidence that a similar conductance is present in human airway epithelial cultures. Like the alveolar subphase fluid, the liquid lining the apical surface of the airways is acidic. Acidification of this fluid may also exacerbate asthma attacks. Acid secretion across the epithelium is stimulated by histamine or ATP and was inhibited by $ZnCl_2$, but not by amiloride, ouabain, bafilomycin A1, or Sch-28080 (a gastric $K^+$-$H^+$-ATPase inhibitor). Thus, an Hv1 voltage-gated proton channel may secrete acid into this fluid exacerbate asthma attacks. Therefore, increased or defective Hv1 function could be related to airway surface acidification and asthma attacks and cystic fibrosis, and decreased or corrected Hv1 function could be therapeutic.

Maintenance of Acidity/Alkalinity

Because the Hv1 channel functions to pump protons across a cell membrane, its activity has the effect of increasing intracellular pH (i.e., increasing intracellular alkalinity), and decreasing extracellular pH (i.e., increasing extracellular acidity). The effect of pH on the different cells and tissues of the body is a varied as the cells and tissues themselves. For example:

Renal tubular acidosis (RTA) is a disease that occurs when the kidneys fail to excrete acids into the urine, which causes the subject's blood to remain too acidic. Without proper treatment, chronic acidity of the blood leads to growth retardation, kidney stones, bone disease, and progressive renal failure. An Hv1 antagonist, which blocks or reduces acid secretion in endothelial cells, would be expected to be useful for treating or preventing RTA or related conditions, such as kidney stones.

Gallstones can form in the gall bladder due to insufficiently acidic conditions. An Hv1 agonist, which increases acid secretion into the gallbladder, would be expected to be useful for treating or preventing gallstone formation.

Changes in the acidic environment created by anoxic or infected tissues, and thus changes in acid-related pain sensing in inflammatory or anoxic conditions (angina, stroke, diaphragmatic ischemia, pain associated with infection) can be affected by Hv1 channel activity. Therefore, depending upon the need to increase or decrease the acidic environment, an Hv1 agonist or antagonist might be expected to be useful for the treatment of such conditions.

The Hv1 channel also may play a role in intracellular alkalinization following acid loading. Intracellular acidification can result from multiple metabolic and pathophysiological stimuli. Hv1-mediated H+ efflux serves to reduce intracellular [$H^+$], especially when acidic load is paired with membrane depolarization. Therefore, an Hv1 agonist, which increases acid secretion and reduces intracellular acidity, would be expected to be useful for treating such a condition.

Prolonged anaerobic exercise and ischemic events can lead to localized and/or systemic (plasma) acidosis. Acidosis of the muscles can cause muscle pain and injury, and plasma acidosis can result in cardiac arrhythmias and respiratory decompensation. Therefore, modulators of Hv1 activity would be expected to be useful for treating such conditions.

Proton extrusion into an extracellular resorption compartment is an essential component of bone degradation by osteoclasts, and an imbalance of osteoclastic resorption over osteoblastic bone formation results in bone loss and osteoporosis. Chronic acidosis is known to induce negative calcium balance and bone loss by stimulating osteoclastic bone resorption. Therefore, an Hv1 antagonist, which decreases acid secretion, would be expected to be useful for treating this condition.

In patients with healthy kidney function, increased Hv1 activity would be expected to result in increased clearance of acid load due to anoxia, tissue injury, or overwhelming infection. Increased acid secretion by the kidney also would be expected to be useful in preventing chronic bladder infections.

If Hv1 is expressed in the lining of the stomach, Hv1 antagonists would be expected to be useful in the treatment of excessive gastric acid secretion.

Because many pain-sensing neurons are, in fact, acid-sensing neurons, reduction in extracellular acidity can have an analgesic effect. Therefore, Hv1 antagonists would be expected to be useful in the treatment of pain.

Altitude Sickness

Altitude sickness, also known as acute mountain sickness (AMS), is a pathological condition caused by acute exposure to high altitudes (greater than 2,400 meters or 8000 feet). Acute mountain sickness can progress to high altitude pulmonary edema (HAPE) or high altitude cerebral edema (HACE). An Hv1 agonist may be useful to treat or prevent altitude sickness.

Methods of Treating Hv1-Mediated Disease or Disorder.

In another aspect, the present invention provides methods of treating a disease or disorder in Hv1-deficient subjects, in which an enhancer of Hv1 expression or an agonist of Hv1 activity is administered to the subject. In other embodiments, gene or protein therapy can be employed to provide the Hv1 gene or protein to immune tissue which is deficient in the Hv1 gene or protein. For gene therapy, a genetic construct encoding a Hv1 protein can be employed to cause expression of a Hv1 protein in immune tissue which is deficient in the Hv1 gene or protein.

Modulators of Hv1 activity that are Hv1 agonists increase acid secretion from a cell containing Hv1 protein, thereby increasing the pH of the cell. Thus, agonists of Hv1 activity can be used to treat or prevent any disease or condition that is related to increased cell acidity.

Modulators of Hv1 activity that are Hv1 antagonists decrease acid secretion from a cell containing Hv1 protein, thereby increasing the pH of the cell. Thus, antagonists of Hv1 activity can be used to treat or prevent any disease or condition that is related to increased cell alkalinity.

EXAMPLES

The following examples illustrate some specific modes of practicing the present invention, but are not intended to limit the scope of the claimed invention. Alternative materials and methods can be utilized to obtain similar results.

Sequence Alignments

Protein sequences of Hv1 protein species orthologues were either identified using BLAST searches or by searching NCBI for sequences bearing an HVCN1 annotation. Protein sequences were derived by in silico translation of open reading frames present in HVCN1-like transcripts found in the NCBI database. Hv1 protein sequence alignment from different species is shown in FIG. 2.

Mutagenesis

Human Hv1 cDNA was amplified by polymerase chain reaction (PCR) from an expressed sequence tag clone (IMAGE 6424182) and subcloned into pQBI25-fC3 (QBiogene) to create GFP-hHv1, into pcDNA3.1(−) for expression of non-tagged Hv1, or into pBSIISK (−) (Stratagene, La Jolla, Calif.) for in vitro mRNA transcription. Site-directed mutagenesis (using QuickChange® Site-Directed Mutagenesis Kit from Stratagene, a Jolla, Calif.) was used to create point mutations in GFP-hHv1. A C-terminal HA tag (a synthetic peptide corresponding to amino acid residues 98-106 (YPYDVPDYA) of human Influenza virus hemagglutinin) was added by PCR to create hHv1-HA; expression of transfected hHv1-HA was detected in immunoblots using an anti-HA antibody. A ~300 nucleotide antisense RNA probe labelled with a-$^{33}$P-UTP was synthesized by in vitro transcription (Ambion, An Applied Biosystems Business, Austin, Tex.) and hybridized (68° C.) to a human multiple tissue mRNA panel (MTE3, Clontech, Mountain View, Calif.). Incorporated radioactivity was detected by a phosphorimager (Molecular Dynamics). Currents reported here were recorded 18-36 hr after transfection of GFP-hHv1 cDNA in the HEK-293 cell clone HM1, which stably expresses the human muscarinic M1 receptor1 (see Peralta et al. (1988), Nature 334: 434-7); essentially identical results were obtained when Hv1 was expressed in either HEK-293 or COS-7 cells. Recording solutions were similar to those described by Morgan et al. (2002), *J. Gen. Physiol.* 119: 571-580, and contained 100 mM pH buffer (MES, Bis-Tris or HEPES), near its pKa (5.5, 6.5 or 7.5, respectively) in tetramethylammonium methanesulphonate or NaCl adjusted to ~300 mOsm. H+ gradients ($pH^+_{i/o}$ = $[H+]_{intracellular}/[H+]_{extracellular}$) were imposed by gravity-fed bath superfusion of differentially buffered solutions. Currents were recorded with an Axopatch 200A (Axon Instruments; 1 kHz filter) and digitized at 2 kHz (10 kHz for Arg mutants) using Clampex9 (Axon Instruments). Data were analyzed using Clampfit9 (Axon Instruments) and Origin 6 (Microcal). Recordings were performed at 22-24° C. unless otherwise stated.

Results of mutagenesis experiments are shown in Table 1.

TABLE 1

| Phenotype | Point mutation | | Deletion/Substitution |
|---|---|---|---|
| Functional | F96G | S143A | H167-K169→NVN |
| | F166C | K157A[a] | H167-K169→DEC |
| | F170C | D185A | Q191-H193→DEW |
| | I183C | S181A | |
| | F195C | E164A/E171A | |
| | D112H[a] | E192A/E196A | |
| | D112E | N214H | |
| | K125A/K131A | | |
| | D123A/D130A | | |
| | N214D | | |
| Functional with faster activation kinetics | R205A | G199C* | Deletion of K221-N273 |
| | R208A | | |
| Functional with slower activation kinetics | R211A | | |
| Functional, but voltage-dependent activation is shifted toward negative $V_m$ | E153A | R205Q | |
| | E153D | D174A | |
| Functional, but voltage-dependent activation is shifted toward positive $V_m$ | R162A | R205S | |
| | R205A | R208A | |
| | R205C | R211A | |
| Not functional | D112A[b] | D112A/R205A | |
| | D112C | D112A/R205C | |
| | D112K | D112A/R205S | |
| | D112R | N214R[b] | |
| | D112A/E119A | N214K | |

TABLE 1-continued

| Phenotype | Point mutation | Deletion/Substitution |
|---|---|---|
| No expression observed | N133C | |
| $Zn^{2+}$ sensitivity decreased | H140A | H193A |
| | H140A/H193A | |

[a]Mutations express small H+ currents in HEK cells
[b]Residues expressed on plasma membrane in 293T cells (biotinylation)
*Reactivity of G199C (but not wt hHv1) with membrane-impermeant sulfhydryl-reactive agents like MTSET [2-(trimethylammonium)methanethiosulfonate] indicates that a) the top of the S4 domain is accessible to the extracellular environment and b) reactivity of Cys engineered into this position could be used as a way to measure Hv1 function independently from- electrophysiology or pH-sensitive dye imaging. [THIS COULD BE MOVED TO A LATER EXAMPLE]

Expression of Mutant hHV1 Proteins on Plasma Membrane 293T cells (obtained from American Type Culture Collection (ATCC), Manassas, Va.) were transiently transfected with the mutated human Hv1 cDNA sequence and removed from substrate by gentle trituration in $Ca^{2+}$-free D-PBS 24 hours later. Cell suspensions were incubated 2 hr at 4° C. with gentle rocking in D-PBS containing 1 mg/ml NHS-biotin (Pierce, now Thermo Fisher Scientific, Waltham, Mass.). After one wash (500×g, 10 min at 4° C.) biotin was quenched with 50 mM glycine in D-PBS (15 min at 4° C.) and cells were washed 3 more times. Cell pellets were snap frozen in liquid $N_2$, stored at −80° C., and later lysed in D-PBS+1% TX100+ protease inhibitors (Roche). After centrifugation (10 min at 4° C., 15,000×g) to clear detergent-insoluble material, 50 ml Neutravidin (Pierce) slurry was added and lysates incubated 3 hr at 4° C. with gentle rocking. Beads were collected by centrifugation (1,000×g, 5 min at 4° C.) and the supernatant saved as intracellular fraction. After two more washes, protein was eluted from beads in Nu-PAGE LDS loading buffer (Invitrogen), subjected to SDS-PAGE, and transferred to a PDVF membrane. The blot was incubated with an anti-GFP mAb (Covance, 1:2,000), washed, and probed with an anti-mouse HRP-conjugated secondary Ab (Zymed, 1:40,000) and proteins were detected by chemiluminescence (ECL Dura, Pierce). The results confirmed that D112A and N214R hHv1 mutants are expressed on the plasma membrane.

C-terminal Truncation of hHv1 Protein

According to procedures outlined above, a mutant with the deletion of the C-terminal portion of the protein (KC211-N273) was prepared. Patch-clamp methods outlined above indicated that the mutant was functional, with slightly faster activation kinetics compared to the wild-type hHv1 protein.

Screening Assay For Modulators of hHv1 Activity with a G199C Mutant hHv1 Protein The Cys residue in a G199C mutant hHv1 protein is covalently reacted with a fluorophore coupled to a maleimide compound (e.g., rhodamine maleimide). When the fluorophore moves into the membrane lipid environment, quenching occurs which can be measured as changes in fluorescence. Exemplary protocols can be found in Cha et al. (1997), Neuron 19:1127-1140; Sorensen et al. (2000) J. Gen. Physiol. 115: 209-221; Blunck et al. (2004) Biophys. J. 86: 3966-3980; Cha et al. (1999) Nature 402: 809-813; and Cha et al. (1998) J. Gen. Physiol. 112: 391-408.

The ability of MTSET (2-(trimethylammonium)methanethiosulfonate), which is a sulfhydryl-reactive agent, to modulate hHv1 currents demonstrates that Cys at position 199 is accessible to covalent modification by maleimide reagents. There is little effect of MTSET on wt GFP-hHv1 currents, so the reactivity of MTSET is specific to the engineered Cys at residue 199. This concept is demonstrated in FIG. 3.

Hv1 Transgenic Knockout Animals

The Bay Genomics embryonic stem (ES) cell clone RRN293 (Mutant Mouse Region Resource Center, U C Davis, Davis, Calif.) was used to generate Hv1 knockout mice. The Bay Genomics strategy is to randomly introduce transgenic plasmid DNA into mouse ES cells at low frequency. The transgenic DNA contains a splice acceptor site that will allow for the creation of a novel transgenic mRNA if the vector is inserted into an intronic sequence of a gene. mRNA transcribed from trapped alleles contain coding sequence from one or more 5'-exons fused to a β-galactosidase/Neomycin (β-Geo) cassette. The resultant mRNA contains the desired transgene-specific sequence followed in frame by a β-Geo sequence and therefore encodes a fusion protein that can be used as a reporter for the transgene's expression. Trapped alleles result from splicing of the genetrap vector into the genomic loci of random genes and are preserved in the form of ES cell clones. Standard techniques for creating knockout mice are followed to make transgenic genetrap mouse strains. Briefly, ES cells are injected into mouse blastocysts and implanted into pseudo-pregnant mothers, resulting in chimeric pups. Chimeric male mice producing sperm cells bearing the trapped allele produce heterozygous transgenic offspring (e.g., wt/RRN293) when bred with wt/wt females, and the heterozygous mice are bred to produce homozygous transgenic mice (e.g., RRN293/RRN293).

FIG. 4 shows a schematic overview of HVCN1 genetrap. The Bay Genomics database (http://baygenomics.ucsf.edu/cgi-bin/BayDbAccess.py?TYPE=search) was searched for sequence tags containing HVCN1 sequence and identified clone RRN293 as a putative HVCN1 genetrap. A series of genomic primers were designed to locate the insertion site by PCR using transgene-specific and β-Geo primers. Genoptypes of mice were then determined in triplex PCR reactions containing both wt and β-Geo primers and genomic DNA purified from mouse tails. β-Geo reporter expression may be used to track Hv1 protein expression in heterozygous or homozygous RRN293 mice.

A Bay Genomics HVCN1 genetrap vector was inserted into an intronic sequence of the murine HVCN1 gene as shown in FIG. 4. In the trapped HVCN1 allele, DNA encoding β-Geo follows exon 1 (non-coding) and exon 2 (encoding amino acids 1-6). The translated Hv1-β-Geo fusion protein therefore contains only the N-terminal 6 amino acids of the Hv1 polypeptide and is thus nonfunctional with respect to H+ channel activity. Homozygous RRN293/RRN293 transgenic animals are functional Hv1 knockouts, with the Hv1-β-Geo fusion protein expressed under the control of the native HVCN1 promoter. Chimeric male RRN293 transgenic mice were produced from RRN293 cells introduced within C57/BL6J blastocysts. The chimeric RRN293 males were crossed with wt females to produce germline-transmitted heterozygous RRN293 animals. Mating heterozygotes yields a mixture of wt, RRN293 homozygous, and RRN293 heterozygous animals whose genotype was determined by quantitative genomic PCR using primers specific for wt HVCN1 or β-Geo sequences. A triplex genomic PCR strategy using different primers was used to confirm genotypes and was able to unambiguously identify wt/wt, wt/RRN293 and RRN293/RRN293 animals. RRN293/RRN293 mice are morphologically normal to date (~9 months age) and visually indistinguishable from wt/wt or wt/RRN293 littermates.

In order to determine whether Hv1 function was ablated in RRN293/RRN293 mice, voltage-gated $H^+$ currents were measured in purified granulocytic leukocytes isolated from wt/Wt or RRN293/RRN293 mice. Voltage-dependent $H^+$ currents of varying magnitude were readily recorded in wt/wt cells but were undetectable in RRN293/RRN293 cells, confirming the effectiveness of the RRN293 transgene to knock out Hv1 protein function.

Voltage-Gated H+ Currents are Absent from RRN293/RRN293 Mouse Leukocytes

Whole-cell currents were measured in granulocytic leukocytes purified from wt/wt or RRN293/RRN293 mouse peripheral blood by density gradient centrifugation (Robbins PMN) using solutions (100 mM Bis-Tris, 80 mM NaCl, 1 mM EGTA, pH 6.5 or 100 mM HEPES, 80 in M NaCl, 1 mM EGTA, pH 7.5) as previously described by Ramsey et al (Ramsey et al. (2006), supra). The results are shown in Table 2.

TABLE 2

| Genotype | Mean Hv1 current | s.e.m. Hv1 current | n |
| --- | --- | --- | --- |
| wt/wt | 58.6 | 10.5 | 14 |
| RRN293/RRN293 | 2.7 | 0.4 | 14 |
| $P < 0.0001$, t-test | | | |

Hv1 Protein Expression in Mice

Immunocytochemistry was performed using an affinity-purified SulfoLink (Pierce) rabbit polyclonal anti-peptide (CLDLKIIEPDEQDYA; SEQ ID NO: 23) antiserum (4232-3, Chemicon, now part of Millipore, Billerica, MA) to visualize Hv1 protein expression. Specific Hv1 immmunoreactivity was absent from bone marrow leukocytes of RRN293/RRN293mice and wt/wt cells incubated with the primary antibody +antigenic peptide, indicating that the RRN293transgene eliminates detectable expression of Hv1 protein. The utility of this antibody was confirmed in primary mouse bone marrow cells and transfected HEK-293cells. No staining was seen in the presence of primary antibody plus antigenic peptide or in the absence of primary antibody, but robust staining was seen in $gp91^{phox}$-positive (as assessed using 7D5 mAb, Medical & Biological Laboratories, Woburn, MA) bone marrow leukocytes and in HEK-293 cells expressing GFP-hHv1.

Hematological Analysis of Mice

Figure 5:
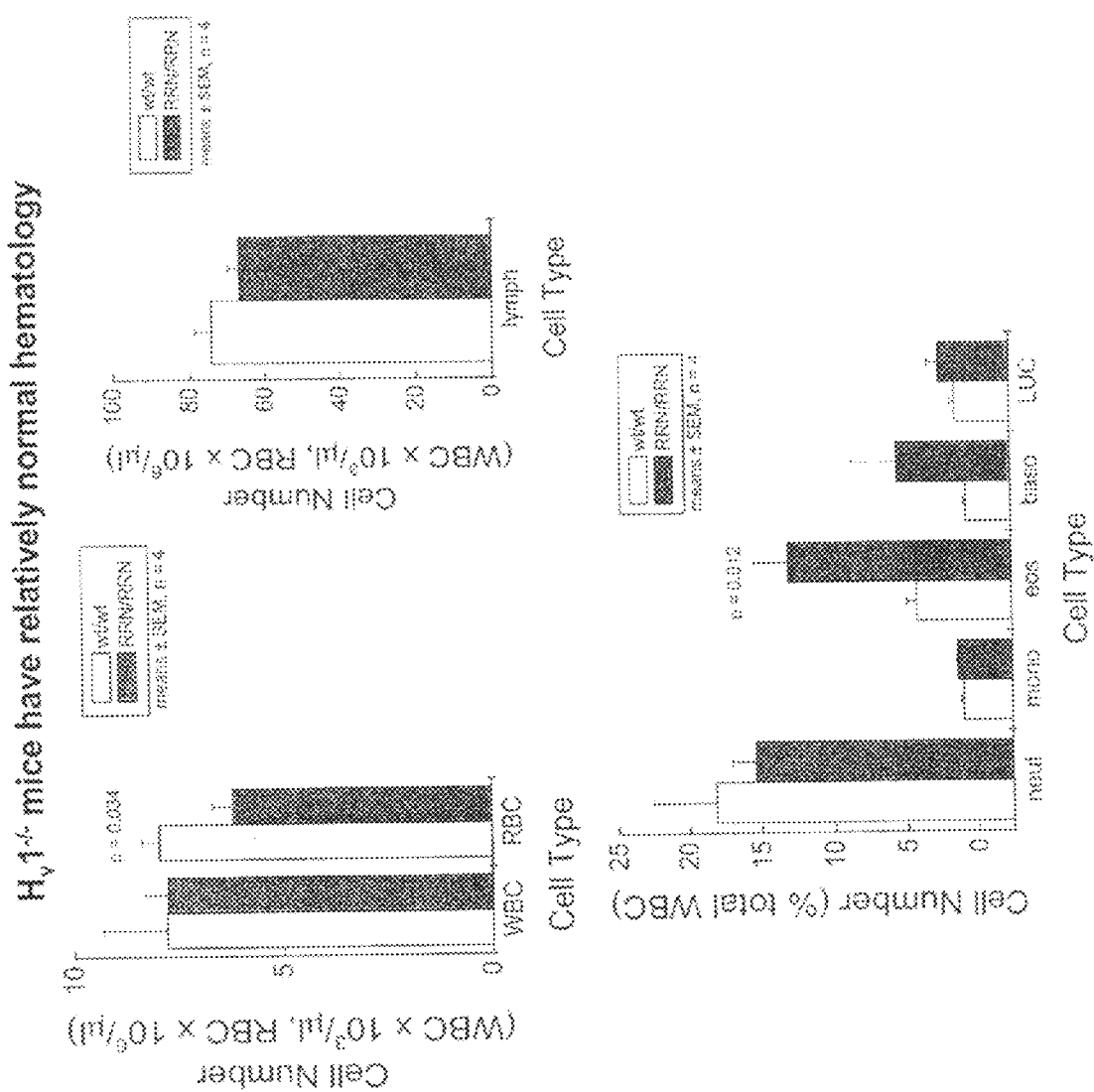
FIG. 5 shows the hematology of wild-type and Hv1−/− mice.

Standard complete blood counts (CBC) and differential white cell counts performed on whole peripheral blood revealed a modest increase in the number of eosinophils in RRN293/RRN293 mice compared to age-matched wt/wt controls but no change in the numbers of erythrocytes or other leukocytes as shown in FIG. 5. This demonstrates that Hv1 knockout does not significantly perturb the production or maturation of cellular blood components in mice.

Hv1 Protein Expression in Mouse Bone Marrow Leukocytes

Immunocytochemistry demonstrates expression of Hv1 protein in wt mouse bone marrow leukocytes. Cells were freshly isolated from bone marrow in ice-cold D-PBS, washed by centrifugation, and resuspended in standard Ringer's solution (138 mM NaCl, 5 mM KCl, 1.8 mM $CaCl_2$, 1 mM $MgCl_2$, 10 mM HEPES, pH 7.4) and plated onto glass coverslips (60 min, 37° C.). Cells were fixed (4% paraformaldehyde +0.15 M sucrose in D-PBS or Ringer's solution; 15 min, 24° C.), permeabilized (0.2% Triton X-100 in D-PBS; 15 min, 24° C.), and blocked (2% BS+2% FBS+2% fish gelatin in D-PBS or Ringer's solution or 10% goat serum in D-PBS; 30 mM at 24° C.) sequentially by aspiration and replacement of 75 ml aliquots of each solution. No differences in straining were observed when using either D-PBS or Ringer's solutions. Cells were incubated (a) without primary antibody, (b) with anti-Hv1 primary antibody (4232-3, 1.5 mg/ml), (c) with 4232-3 (1.5 mg/ml) in the presence of antigenic peptide (3 mg/ml), or (d) with an anti-gp91phox mouse monoclonal antibody (7D5, 1:1000) for 60 min 24° C. and washed twice with D-PBS or Ringer's solution. Secondary antibody cocktail (Alexa 488-conjugated goat anti-rabbit and Alexa 647-conjugated goat anti-mouse (Invitrogen, Carlsbad, Calif.), each at 1:3,000) was added for 60 min, 24° C. and washed twice with D-PBS or Ringer's solution. Cells were dried and mounted onto glass slides in Fluoromount G preservative. All reagents were diluted freshly from stocks stored at −20° C. or −80° C. and used immediately. Images were acquired on an Olympus Fluoview 300 or Fluoview 1000 confocal microscope using either 488 nm or 633 nm laser illumination to visualize fluorescence. Fluorescence emission intensity with 488 nm excitation or 633 nm excitation was measured. The results show that cells incubated with 4232-3 primary antibody exhibit intense fluorescence in a subpopulation of bone marrow leukocytes under 488 nm excitation, demonstrating Hv1 expression in these cells. Only weak background-level fluorescence is observed in cells incubated with the secondary antibody alone or when 4232-3 was incubated with the antigenic peptide, indicating that the fluorescence signal observed with 4232-3 alone is specific for Hv1 protein. A majority of the bone marrow cells incubated with 7D5 exhibit strong fluorescence signals under 633 nm excitation, identifying them as phagocytes When the secondary antibody used in the above experiment was Alexa 647-conjugated goat anti-rabbit (1:3,000), the Hv1 protein expression in RRN293/RRN293 mouse bone marrow leukocytes was shown to be abolished.

Superoxide Production in Primary Mouse Bone Marrow Leukocytes

Amplex Ultra Red assay (Invitrogen) was used to measure hydrogen peroxide ($H_2O_2$) production in primary mouse bone marrow leukocytes. $H_2O_2$ is generated spontaneously when superoxide ($O_2^-$) secreted by cells reacts with $H_2O$. Thus the Amplex Ultra Red assay is a convenient proxy for direct measurement of $O_2^-$ production. Freshly isolated bone marrow cells from (a) wt/wt or (b) RRN293/RRN293 mice were incubated for the indicated time at 37° C. Absorbance at 540 nm was measured on a plate-reading spectrophotometer. Nine animals of each genotype were tested in two separate experiments. Each condition was measured in triplicate wells on a 96-well plate and the average of these triplicate values were then averaged across multiple animals. The assay contained $5 \times 10^5$ cells and 100 µM Aplex Ultra Red in a final volume of 200 ml. Drug additions included phorbol-12-myristate-13-acetate (PMA, 200 nM), used to activate NADPH oxidase system, in the absence and presence of either the NADPH oxidase inhibitor diphenylene iodonium (DPI, 10 µM) or Hv1 inhibitor $Zn^{2+}$ (in the form of $ZnCl_2$, 1 mM) to assess the relative contribution of oxidase-dependent and Hv1-dependent mechanisms to $O_2^-$ production. Cells (20 ml, $1 \times 10^7$.ml-1) in ice-cold Ringer's were added to the wells and zero time measurements were made immediately after removing the plate from ice. The reaction was initiated by placing plated in an air-heated incubator (37° C.). Plates were briefly removed (<2 mins.) from the incubator and absorbance or fluorescence was measured at the indicated time points. At 90 mins., PMA-stimulated and DPI-sensitive superoxide production was decreased 71.0±2.7% in RRN293/RRN93 cells compared to wt/wt cells (mean±S.E.M., n=9 mice each; ** p <1×10$^{-6}$ by Student's unpaired t-test). Results demonstrate that Hv1 expression is necessary for normal rate of superoxide production in leukocytes.

NADPH Oxidase-Dependent Killing of *Staphylococcus aureus* by Mouse Bone Marrow Cells Freshly isolated mouse bone marrow cells (1×10$^6$) were incubated on ice (450 ml in round-bottom polypropylene tubes) standard Ringer's solution in the absence or presence of DPI (10 mM). *S. aureus* (1×10$^6$ CFU in 50 ml Ringer's) were added and tubes were transferred to a heated shaking incubator (37° C., 100 cycles·min$^{-1}$) for 30 min. Gentamicin was added to a final concentration of 50 µg/ml and cells were pelleted by centrifugation (10 min at 3,000×g) and washed once with Ringer's solution (10 min at 3,000×g). Pellets were resuspended in 1% saponin solution, frozen (−80° C.), and thawed to liberate intracellular bacteria. *S. aureus* were serially diluted in 0.05% Tween-20, plated on cetrimide agar plates, and grown for 18 hrs. at 37° C. Bacterial Colonies were manually counted and fractional killing was normalized to the number of colonies observed in the presence of DPI.

Figure 6:
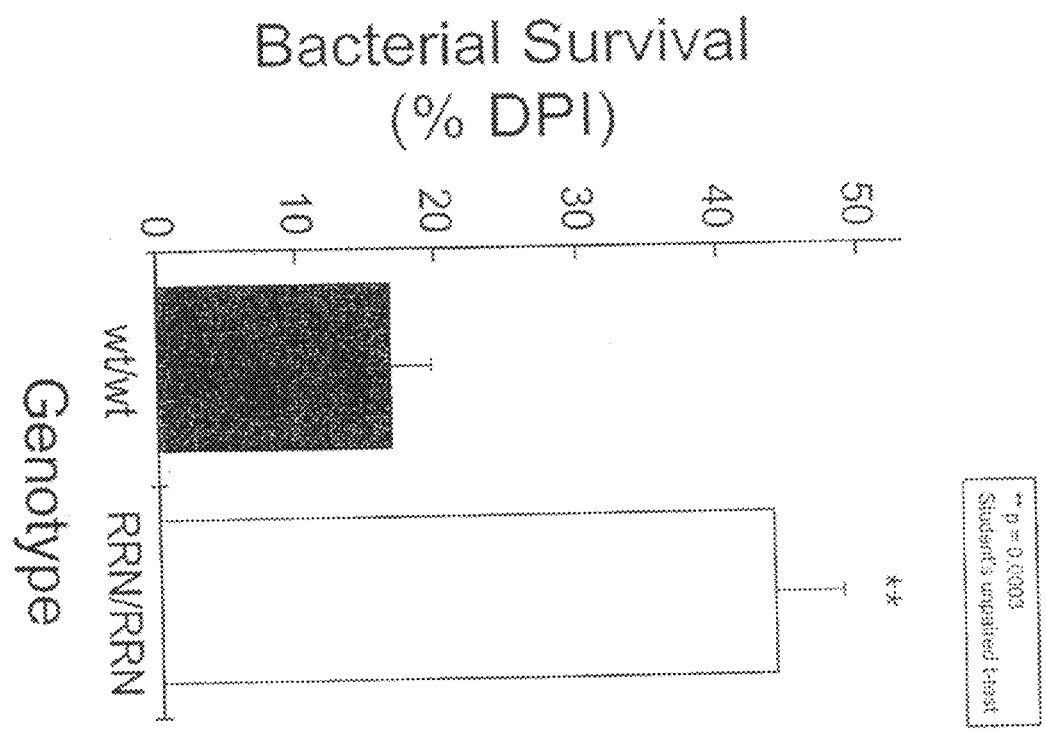
FIG. 6 shows the bacterial survival in wild-type and Hv1−/− mice.

The results, shown in FIG. 6 demonstrate a highly increased rate of *S. aureus* survival in RRN293/RRN293 (i.e., Hv1 deficient) mice compared to the wt mice.

Production of Peptide Antibody.

Antibodies are made to synthetic peptides corresponding approximately to amino acid residues 1-29, 32-68, 78-100, 126-136, 191-199, 221-237 and 241-273 of SEQ ID NO: 2 (or a non-human homolog thereof) with a cysteine attached to the N-terminus. These peptides are conjugated to maleimide-activated KLH according to the manufacturer's protocol (Pierce). Rabbits are immunized (intramuscular injection) and subsequently boosted at regular intervals with 100 µg of KLH-peptide conjugate per injection. Anti-peptide antibodies are affinity purified on the corresponding peptide chromatographic column (SulfoLink, Pierce) using Gentle Binding and Elution™ buffers (Pierce).

EQUIVALENTS

While this invention has been particularly shown and described with references to certain embodiments thereof, it will be understood by those skilled in the art that various changes in form and details can be made therein without departing from the spirit and scope of the invention. Those skilled in the art will recognize, or be able to ascertain using no more than routine experimentation, many equivalents to the specific embodiments of the invention described specifically herein. Such equivalents are intended to be encompassed in the scope of the invention.

We claim:

1. A method of detecting a change in the intracellular pH in a cell, the method comprising:
   (a) obtaining a cell transformed with an exogenous genetic construct comprising a sequence encoding a voltage-gated Hv1 proton channel proton, whereby the cell expresses the Hv1 protein having voltage-gated Hv1 proton channel proton activity;
   (b) changing the intracellular pH in the cell;
   (c) detecting a change in an electrical signal caused by the voltage-gated Hv1 proton channel protein in the cell; and
   (d) determining that there has been a decrease in intracellular pH in the cell based on the detection in (c) of an increase in the electrical signal caused by the voltage-gated Hv1 protein channel, or determining that there has been an increase in intracellular pH in the cell based on the detection in (c) of a decrease in the electrical signal caused by the voltage-gated Hv1 protein channel.

2. The method of claim 1, wherein the exogenous genetic construct is a vector comprising a sequence of:
   (a) SEQ ID NOs: 1, 3, 5, 7, 9, 11, 13, 15, 17, 19 or 21; or
   (b) a fully complementary sequence to any one of the sequences of (a).

3. The method of claim 1, wherein the exogenous genetic construct is a vector comprising a sequence of:
   (a) a sequence encoding a polypeptide of SEQ ID NOs: 2, 4, 6, 8, 10, 12, 14, 16, 18, 20 or 22; or
   (b) a fully complementary sequence to any one of the sequences of (a).

4. The method of claim 1, wherein the sequence encoding the voltage-gated Hv1 proton channel protein is operably joined to a reporter gene.

5. The method of claim 1, wherein the sequence encoding the voltage-gated Hv1 proton channel protein is operably joined to a heterologous coding sequence to encode a fusion protein.

6. The method of claim 1, wherein the cell is selected from the group consisting of a bacterial cell, a yeast cell, an insect cell, a nematode cell, an amphibian cell, and a mammalian cell.

7. The method of claim 1, wherein the exogenous genetic construct is optimized for expression in E. coli.

8. The method of claim 1, wherein the exogenous genetic construct is optimized for expression of the voltage-gated Hv1 proton channel protein on the surface of the cell.

9. The method of claim 6, wherein the mammalian cell is a mammalian cell line.

10. The method of claim 1, wherein the exogenous genetic construct is a vector comprising a sequence that encodes a polypeptide that is at least 80% identical to one of SEQ ID NO: 2, 4, 6, 8, 10, 12, 14, 16, 18, 20 or 22, and has voltage-gated Hv1 proton channel protein activity.

11. The method of claim 1, wherein the exogenous genetic construct is a vector comprising a sequence that encodes a polypeptide that is at least 85% identical to one of SEQ ID NO: 2, 4, 6, 8, 10, 12, 14, 16, 18, 20 or 22, and has voltage-gated Hv1 proton channel protein activity.

12. The method of claim 1, wherein the exogenous genetic construct is a vector comprising a sequence that encodes a polypeptide that is at least 90% identical to one of SEQ ID NO: 2, 4, 6, 8, 10, 12, 14, 16, 18, 20 or 22, and has voltage-gated Hv1 proton channel protein activity.

13. The method of claim 1, wherein the exogenous genetic construct is a vector comprising a sequence that encodes a polypeptide that is at least 95% identical to one of SEQ ID NO: 2, 4, 6, 8, 10, 12, 14, 16, 18, 20 or 22, and has voltage-gated Hv1 proton channel protein activity.

14. The method of claim 2, wherein the vector comprises the sequence of SEQ ID NO: 1.

15. The method of claim 3, wherein the vector comprises a sequence encoding a polypeptide of SEQ ID NO: 2.

16. The method of claim 1, wherein the exogenous genetic construct further comprises a heterologous promoter that is operably linked to the sequence encoding the voltage-gated Hv1 proton channel protein.

* * * * *